(12) United States Patent
Wright et al.

(10) Patent No.: US 8,128,740 B2
(45) Date of Patent: Mar. 6, 2012

(54) DEVICE FOR SEPARATING GAS FROM A LIQUID PATH

(75) Inventors: David Walter Wright, Littleton, CA (US); Jeffrey C. Garland, Littleton, CO (US)

(73) Assignee: Organ Recovery Systems, Inc., Des Plaines, IL (US)

( * ) Notice: Subject to any disclaimer, the term of this patent is extended or adjusted under 35 U.S.C. 154(b) by 1705 days.

(21) Appl. No.: 10/816,252

(22) Filed: Apr. 2, 2004

(65) Prior Publication Data

US 2004/0221719 A1 Nov. 11, 2004

Related U.S. Application Data

(60) Provisional application No. 60/459,981, filed on Apr. 4, 2003.

(51) Int. Cl.
*B01D 19/00* (2006.01)
*A01N 1/00* (2006.01)
*A01N 1/02* (2006.01)

(52) U.S. Cl. ............ 96/155; 96/219; 96/182; 96/183; 96/4; 96/241; 96/156; 435/284.1; 604/319; 210/436; 210/188; 210/472; 210/422

(58) Field of Classification Search .......... 95/241; 96/155, 156, 219, 182, 183, 4; 604/319; 435/284.1; 210/436, 188, 472, 422
See application file for complete search history.

(56) References Cited

U.S. PATENT DOCUMENTS

| | | |
|---|---|---|
| 1,682,344 A | 8/1928 | Lesieur |
| 1,916,658 A | 7/1933 | Davidson |
| 3,406,531 A | 10/1968 | Swenson et al. |
| 3,545,221 A | 12/1970 | Swenson et al. |
| 3,607,646 A | 9/1971 | de Roissart |
| 3,632,473 A | 1/1972 | Belzer et al. |
| 3,639,084 A | 2/1972 | Goldhaber |
| 3,654,085 A | 4/1972 | Norr et al. |
| 3,660,241 A | 5/1972 | Michielsen |
| 3,712,583 A | 1/1973 | Martindale et al. |
| 3,738,914 A | 6/1973 | Thorne et al. |
| 3,753,865 A | 8/1973 | Belzer et al. |
| 3,772,153 A | 11/1973 | de Roissart |
| 3,777,507 A | 12/1973 | Burton et al. |

(Continued)

FOREIGN PATENT DOCUMENTS

WO    WO 86/00812    2/1986

(Continued)

OTHER PUBLICATIONS

U.S. Appl. No. 60/459,981, filed Apr. 4, 2003, David W. Wright et al.

(Continued)

*Primary Examiner* — Nathan Bowers
(74) *Attorney, Agent, or Firm* — Oliff & Berridge, PLC

(57) ABSTRACT

The invention is targeted at the process of separating gas, such as air, from a liquid path. Specifically, the invention provides a means to remove gas from a dynamic liquid path, manage the removed gas and liquid path. The invention provides a means to remove gas from a dynamic liquid path using the buoyant property of gas in a less buoyant liquid, having ingress and egress ports for liquid and gas flow, and separate points of egress for liquid and trapped gas and integral liquid channels.

72 Claims, 12 Drawing Sheets

U.S. PATENT DOCUMENTS

| | | |
|---|---|---|
| 3,810,367 A | 5/1974 | Peterson |
| 3,843,455 A | 10/1974 | Bier |
| 3,845,974 A | 11/1974 | Pelloux-Gervais |
| 3,877,843 A | 4/1975 | Fischel |
| 3,881,990 A | 5/1975 | Burton et al. |
| 3,892,628 A | 7/1975 | Thorne et al. |
| 3,914,954 A | 10/1975 | Doerig |
| 3,935,065 A | 1/1976 | Doerig |
| 3,962,439 A | 6/1976 | Yokoyama et al. |
| 3,995,444 A | 12/1976 | Clark et al. |
| 4,186,565 A | 2/1980 | Toledo-Pereyra |
| 4,231,354 A | 11/1980 | Kurtz et al. |
| 4,242,883 A | 1/1981 | Toledo-Pereyra |
| 4,243,883 A | 1/1981 | Schwarzmann |
| 4,345,919 A | 8/1982 | Wilkinson et al. |
| 4,378,797 A | 4/1983 | Osterholm |
| 4,393,863 A | 7/1983 | Osterholm |
| 4,445,500 A | 5/1984 | Osterholm |
| 4,451,251 A | 5/1984 | Osterholm |
| 4,462,215 A | 7/1984 | Kuraoka et al. |
| 4,471,629 A | 9/1984 | Toledo-Pereyra |
| 4,473,637 A | 9/1984 | Guibert |
| 4,474,016 A | 10/1984 | Winchell |
| 4,494,385 A | 1/1985 | Kuraoka et al. |
| 4,502,295 A | 3/1985 | Toledo-Pereyra |
| 4,559,298 A | 12/1985 | Fahy |
| 4,596,250 A | 6/1986 | Beisang, III et al. |
| 4,618,586 A | 10/1986 | Walker |
| 4,629,686 A | 12/1986 | Gruenberg |
| 4,643,713 A * | 2/1987 | Viitala ............ 604/6.15 |
| 4,657,532 A | 4/1987 | Osterholm |
| 4,666,425 A | 5/1987 | Fleming |
| 4,704,029 A | 11/1987 | Van Heuvelen |
| 4,717,548 A | 1/1988 | Lee |
| 4,723,974 A | 2/1988 | Ammerman |
| 4,734,269 A | 3/1988 | Clarke et al. |
| 4,745,759 A | 5/1988 | Bauer et al. |
| 4,766,740 A | 8/1988 | Bradley et al. |
| 4,801,299 A | 1/1989 | Brendel et al. |
| 4,837,390 A | 6/1989 | Reneau |
| 4,879,283 A | 11/1989 | Belzer et al. |
| 4,951,482 A | 8/1990 | Gilbert |
| 4,958,506 A | 9/1990 | Guilhem et al. |
| 4,976,708 A * | 12/1990 | Oshiyama ............ 604/408 |
| 5,003,787 A | 4/1991 | Zlobinsky |
| 5,013,303 A | 5/1991 | Tamari et al. |
| 5,028,588 A | 7/1991 | Hoffman et al. |
| 5,036,097 A | 7/1991 | Floyd et al. |
| 5,047,395 A | 9/1991 | Wu |
| 5,051,352 A | 9/1991 | Martindale et al. |
| 5,061,236 A * | 10/1991 | Sutherland et al. .......... 604/6.09 |
| 5,066,578 A | 11/1991 | Wikman-Coffelt |
| 5,085,630 A | 2/1992 | Osterholm et al. |
| 5,110,721 A | 5/1992 | Anaise et al. |
| 5,130,230 A | 7/1992 | Segall et al. |
| 5,141,847 A | 8/1992 | Sugimachi et al. |
| 5,145,771 A | 9/1992 | Lemasters et al. |
| 5,149,321 A | 9/1992 | Klatz et al. |
| 5,157,930 A | 10/1992 | McGhee et al. |
| 5,200,176 A | 4/1993 | Wong et al. |
| 5,216,032 A | 6/1993 | Manning |
| 5,217,860 A | 6/1993 | Fahy et al. |
| 5,234,405 A | 8/1993 | Klatz et al. |
| 5,285,657 A | 2/1994 | Bacchi et al. |
| 5,326,706 A | 7/1994 | Yland et al. |
| 5,328,821 A | 7/1994 | Fisher et al. |
| 5,338,662 A | 8/1994 | Sadri |
| 5,356,771 A | 10/1994 | O'Dell |
| 5,362,622 A | 11/1994 | O'Dell et al. |
| 5,383,854 A | 1/1995 | Safar et al. |
| 5,385,821 A | 1/1995 | O'Dell et al. |
| 5,395,314 A | 3/1995 | Klatz et al. |
| 5,434,045 A | 7/1995 | Jost |
| 5,437,633 A | 8/1995 | Manning |
| 5,472,876 A | 12/1995 | Fahy |
| 5,476,763 A | 12/1995 | Bacchi et al. |
| 5,494,822 A | 2/1996 | Sadri |
| 5,584,804 A | 12/1996 | Klatz et al. |
| 5,586,438 A | 12/1996 | Fahy |
| 5,591,251 A | 1/1997 | Brugger |
| 5,599,659 A | 2/1997 | Brasile et al. |
| 5,622,429 A | 4/1997 | Heinze |
| 5,643,712 A | 7/1997 | Brasile |
| 5,674,397 A * | 10/1997 | Pawlak et al. ............. 210/436 |
| 5,681,740 A | 10/1997 | Messier et al. |
| 5,699,793 A | 12/1997 | Brasile |
| 5,702,881 A | 12/1997 | Brasile et al. |
| 5,709,654 A | 1/1998 | Klatz et al. |
| 5,712,084 A | 1/1998 | Osgood |
| 5,716,378 A | 2/1998 | Minten |
| 5,723,282 A | 3/1998 | Fahy et al. |
| 5,730,720 A | 3/1998 | Sites et al. |
| 5,752,929 A | 5/1998 | Klatz et al. |
| 5,821,045 A | 10/1998 | Fahy et al. |
| 5,823,986 A | 10/1998 | Peterson |
| 5,827,222 A | 10/1998 | Klatz et al. |
| 5,843,024 A | 12/1998 | Brasile |
| 5,849,064 A | 12/1998 | Marco et al. |
| 5,856,081 A | 1/1999 | Fahy |
| 5,858,015 A * | 1/1999 | Fini ............................. 604/403 |
| 5,879,329 A | 3/1999 | Ginsburg |
| 5,928,182 A | 7/1999 | Kraus et al. |
| 5,965,433 A | 10/1999 | Gardetto et al. |
| 6,024,698 A | 2/2000 | Brasile |
| 6,046,046 A | 4/2000 | Hassanein |
| 6,100,082 A | 8/2000 | Hassanein |
| 6,673,594 B1 | 1/2004 | Owen et al. |
| 6,677,150 B2 | 1/2004 | Alford et al. |
| 6,918,887 B1 * | 7/2005 | Gremel et al. ............. 604/6.09 |
| 2004/0029266 A1 * | 2/2004 | Barbera-Guillem ....... 435/297.5 |

FOREIGN PATENT DOCUMENTS

| | | |
|---|---|---|
| WO | WO 91/09520 | 7/1991 |
| WO | WO 94/06292 | 3/1994 |
| WO | WO 96/12191 | 4/1996 |
| WO | WO 96/29865 | 10/1996 |
| WO | WO 96/30111 | 10/1996 |
| WO | WO 96/31779 | 10/1996 |
| WO | WO 96/32074 | 10/1996 |
| WO | WO 96/32157 | 10/1996 |
| WO | WO 97/22003 | 6/1997 |
| WO | WO 97/28449 | 8/1997 |
| WO | WO 98/23353 | 6/1998 |
| WO | WO 88/05261 | 7/1998 |
| WO | WO 00/18226 | 4/2000 |
| WO | WO 02/26034 A2 | 4/2002 |

OTHER PUBLICATIONS

U.S. Appl. No. 60/460,875, filed Apr. 8, 2003, David W. Wright et al.
"Randomized Clinical Study of Thiopental Loading in Comatose Survivors of Cardiac Arrest", *The New England Journal of Medicine*, vol. 314, No. 7, pp. 397-403, Feb. 1996.
"Free Radicals and Myocardial Ischemia and Reperfusion Injury", Paul J. Simpson et al., *J Lab Cin Med.*, pp. 13-30, Jul. 1987.
"Development of an Isolated Perfused Dog Kidney With Improved Function", William H. Waugh et al., *American Journal of Physiology*, vol. 217, No. 1, Jul. 1969.
"Variations in Vascular Resistance of Isolated Rat Hearts During Normothermic and Hypothermic Experiments", C.G. Adem et al., *J. Biomed. Engng.*, vol. 3(2), pp. 128-133, 1981.
"Effect of Pharmacologic Agents on the Function of the Hypothermically Preserved Dog Kidney During Normothermic Reperfusion", Rutger J. Ploeg et al., *Surgery*, vol. 103, No. 6, pp. 676-682, Jun. 1988.
"The Beneficial Effect of Intermediate Normothermic Perfusion During Cold Storage of Ischemically Injured Kidneys", Jos G. Maessen et al., *Transplantation*, vol. 47, No. 3, pp. 409-414, Mar. 1989.
"The Asystolic, or Non-Heartbeating, Donor", Gauke Kootstra, *Transplantation*, vol. 63, No. 7, pp. 917-921, 1997.
"Normothermic Renal Artery Perfusion: A Comparison of Perfusates", John D. Hughes et al., *Annals of Vascular Surgery*, vol. 10, pp. 123-130, 1996.
"Is Normothermic Preservation an Alternative to Hypothermic Preservation?", R. N. Dunn et al., *Organ Preservation Basic and Applied Aspects*, Chapter 38, pp. 273-277, 1982.

"Studies of Controlled Reperfusion After Ischemia", Pierre L. Julia, MD et al., *The Journal of Thoracic and Cardiovascular Surgery*, vol. 101, No. 2, pp. 303-313, Feb. 1991.

"Urinary π-Class Glutathione Transferase as an Indicator of Tubular Damage in the Human Kidney", Dr. Anders Sundberg et al., *Nephron*, vol. 67, pp. 308-316, 1994.

"Effect of Ischemia and 24 Hour Reperfusion on ATP Synthesis in the Rat Kidney", E.E. Irazu et al., *Journal of Experimental Pathology*, vol. 4, No. 1, pp. 29-36, 1989.

"Intermediate Normothermic Hemoperfusion of Rat Kidneys: Functional Aspects and a Study Into the Effect of Free Radical Scavengers", A.O. Gaber, *Transplantation Proceedings*, vol. XX, No. 5, pp. 896-898, Oct. 1998.

"Improvement of Postischemic Kidney Function by Reperfusion With a Specifically Developed Solution (BT01)", Pierre Julia, MD et al., *Annals of Vascular Surgery*, vol. 9, pp. S-81-s-88, 1995.

"Ischemia With Intermittent Reperfusion Reduces Functional and Morphologic Damage Following Renal Ischemia in the Rat", Richard S. Frank, MD et al., *Annals of Vascular Surgery*, vol. 7, No. 2, pp. 150-155, 1993.

"Graft Conditioning of Liver in Non-Heart-Beating Donors by an Artificial Heart and Lung Machine In Situ", T. Endoh et al., *Transplantation Proceedings*, vol. 28, No. 1, pp. 110-115, Feb. 1996.

"Machine Perfusion of Isolated Kidney At 37° C. Using Pyridoxalated Hemoglobin-Polyoxyethlene (PHP) solution, UW Solution and Its Combination", T. Horiuchi et al., *Biomaterials, Art. Cells & Immob. Biotech*, vol. 20, Nos. 2-4, pp. 549-555, 1992.

"Analysis of the Optimal Perfusion Pressure and Flow Rate of the Renal Vascular Resistance and Oxygen Consumption in the Hypothermic Perfused Kidney", R. Grundmann, M.D. et al., *Surgery*, vol. 77, No. 3, pp. 451-461, Mar. 1975.

"An Experimental Model for Assessment of Renal Recovery From Warm Ischemia", Paula Jablonski et al., *Transplantation*, vol. 35, No. 3, pp. 198-204, Mar. 1983.

B.G. Rijkmans et al., "Six-Day Canine Kidney Preservation, Hypothermic Perfusion Combined with Isolated Blood Perfusion," Feb. 1984, pp. 130-134.

"Intermediate Normothermic Perfusion During Cold Storage of Ischemically Injured Kidney," J.G. Maessen et al., Transplantation Proceedings, vol. 21, No. 1, Feb. 1989, pp. 1252-1253.

\* cited by examiner

DEVICE FOR SEPARATING GAS FROM A LIQUID PATH

This application is a non-provisional application claiming priority to provisional U.S. Patent Application No. 60/459,981 filed Apr. 4, 2003.

BACKGROUND OF THE INVENTION

The invention relates to an apparatus and method for the process of separating gas from a liquid path.

Perfusion circuits used to perfuse organs, tissues or the like (hereinafter generally referred to as organs) should be free of agents that can create emboli. These emboli are often comprised of gases such as air. Typically emboli range in volume between 1 ml and 0.01 ml but are not limited to these sizes. Gases may be introduced into perfusion circuits through leaks in the circuits, but are more often the result of bubbles trapped in components and geometric facets of the circuits. Gases may also be drawn out of the perfusion liquid by negative pressure due to liquid dynamics, cavitations and eddies and velocity changes throughout the liquid path.

SUMMARY OF THE INVENTION

It is desirable to separate bubbles from a perfusion liquid utilizing the buoyancy of the bubbles with respect to the liquid.

Embodiments of this invention provide systems and methods that separate gases from a liquid path, particularly useful in helping preserve organs and tissues for storage and/or transport.

Embodiments of this invention provide systems and methods to remove gases from a dynamic liquid path and manage the removed gases and liquid path.

Embodiments of this invention provide a means to remove gases from a dynamic liquid path using the buoyant property of the gases in a less buoyant liquid using ingress and egress ports for liquid and gas flow located on substantially the same plane.

Embodiments of this invention provide separate points of egress for liquid and gases.

Embodiments of this invention provide liquid channels formed by housing halves to substantially reduce sharp corners for gas entrapment.

Embodiments of this invention provide an organ cassette which allows an organ to be easily and safely moved between apparatus for perfusion, storing, analyzing and/or transporting the organ. The organ cassette may be configured to provide uninterrupted sterile conditions and efficient heat transfer during transport, recovery, analysis and storage, including transition between the transporter, the perfusion apparatus and the organ diagnostic apparatus.

Embodiments of this invention provide systems and methods for transporting an organ in a transporter, especially for transport over long distances. The organ transporter may be used for various organs, such as the kidneys, and may be adapted to more complex organs such as the liver, having multiple vascular structures, for example the hepatic and portal vasculatures of the liver. The organ transporter may include features of an organ perfusion apparatus, such as sensors and temperature controllers, as well as cassette interface features.

These and other features and advantages of this invention are described in, or are apparent from, the following detailed description of various exemplary embodiments of systems and methods according to this invention.

BRIEF DESCRIPTION OF THE DRAWINGS

These and other aspects and advantages of the invention will become apparent from the following detailed description of embodiments when taken in conjunction with the accompanying drawings, in which.

DETAILED DESCRIPTION OF PREFERRED EMBODIMENTS

Figure 1A:
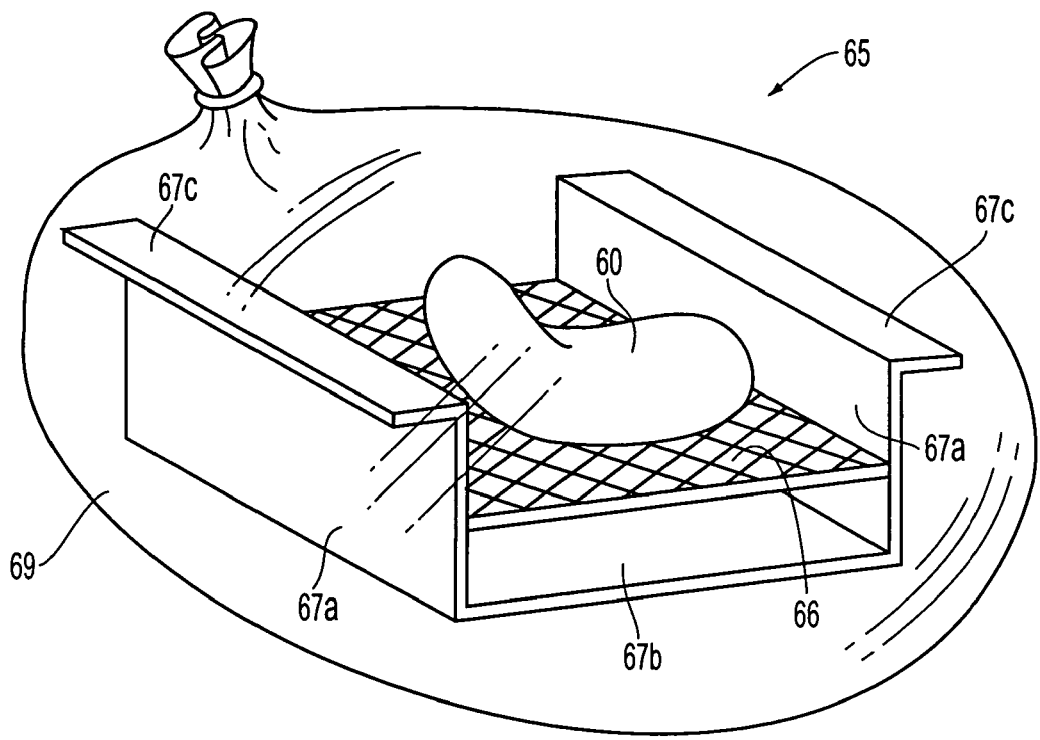
FIGS. 1A-1D shows perspective views of various embodiments of an organ cassette according to the invention.
Figure 1B:
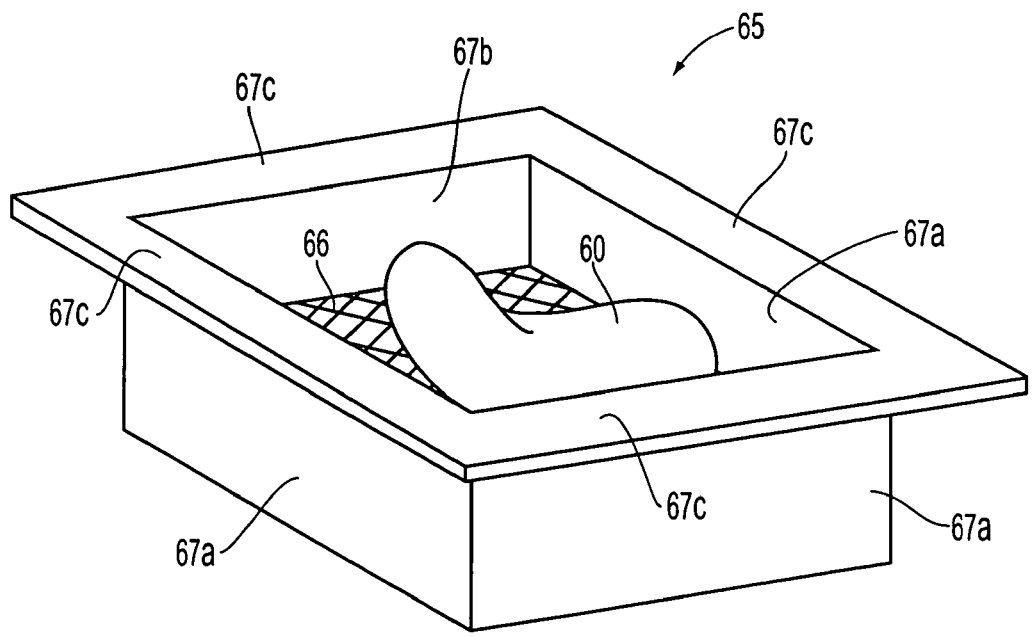

For a general understanding of various features of the invention, reference is made to the drawings. In the drawings, like reference numerals have been used throughout to designate like elements.

The invention is described herein largely in the context of apparatus and methods involved in transport, storage, perfusion and diagnosis of tissues and organs. However, the inventive apparatus and methods have many other applications, and thus the various inventive structures, devices, apparatus and methods described herein should not be construed to be limited to, particular contexts of use. Various features of the disclosed invention are particularly suitable for use in the context of, and in conjunction and/or connection with the features of the apparatus and methods disclosed in U.S. patent application Ser. No. 09/645,525, the entire disclosure of which is hereby incorporated by reference herein.

FIG. 1 shows a cassette 65 which holds an organ 60 to be perfused. Various embodiments of the cassette 65 are shown in FIGS. 1A-1D. The cassette 65 is preferably formed of a material that is light but durable so that the cassette 65 is highly portable. The material may also be transparent to allow visual inspection of the organ.

Preferably the cassette 65 includes side walls 67a, a bottom wall 67b and an organ supporting surface 66, which is preferably formed of a porous, perforated or mesh material to allow liquids to pass therethrough. The cassette 65 may also include a top 67d and may be provided with an opening(s) 63 for tubing (see, for example, FIG. 1D). The opening(s) 63 may include seals 63a (e.g., septum seals or o-ring seals) and optionally be provided with plugs (not shown) to prevent contamination of the organ and maintain a sterile environment. Also, the cassette 65 may be provided with a closeable and/or filtered air vent 61 (see, for example, FIG. 1D). Additionally, the cassette 65 may be provided with tubing for connection to an organ and/or to remove medical liquid from the organ bath, and a connection to an organ and/or to remove medical liquid from the organ bath, and a connection device(s) 64 for connecting the tubing to, for example, tubing 50c, 81, 82, 91 and/or 132, (see, for example, FIG. 1D) of an organ storage, transport, perfusion and/or diagnostic apparatus.

The cassette 65, and/or the organ support, opening(s), tubing(s) and/or connections(s), may be specifically tailored to the type of organ and/or size of organ to be perfused. Flanges 67c of the side support walls 67a can be used to support the cassette 65 disposed in an organ storage, transport, perfusion and/or diagnostic apparatus. The cassette 65 may further include a handle 68 which allows the cassette 65 to be easily handled, as shown, for example, in FIGS. 1C and 1D. Each cassette 65 may also be provided with its own mechanism (e.g., stepping motor/cam valve 75 (for example, in the handle portion 68, as shown in FIG. 1C)) for fine tuning the pressure of medical liquid perfused into the organ 60 disposed therein, as discussed in more detail below. Alternatively, pressure may, in embodiments, be controlled by way of a pneumatic chamber, such as an individual pneumatic chamber for each organ (not shown), or by any suitable variable valve such as a rotary screw valve or a helical screw valve.

Figure 2A:
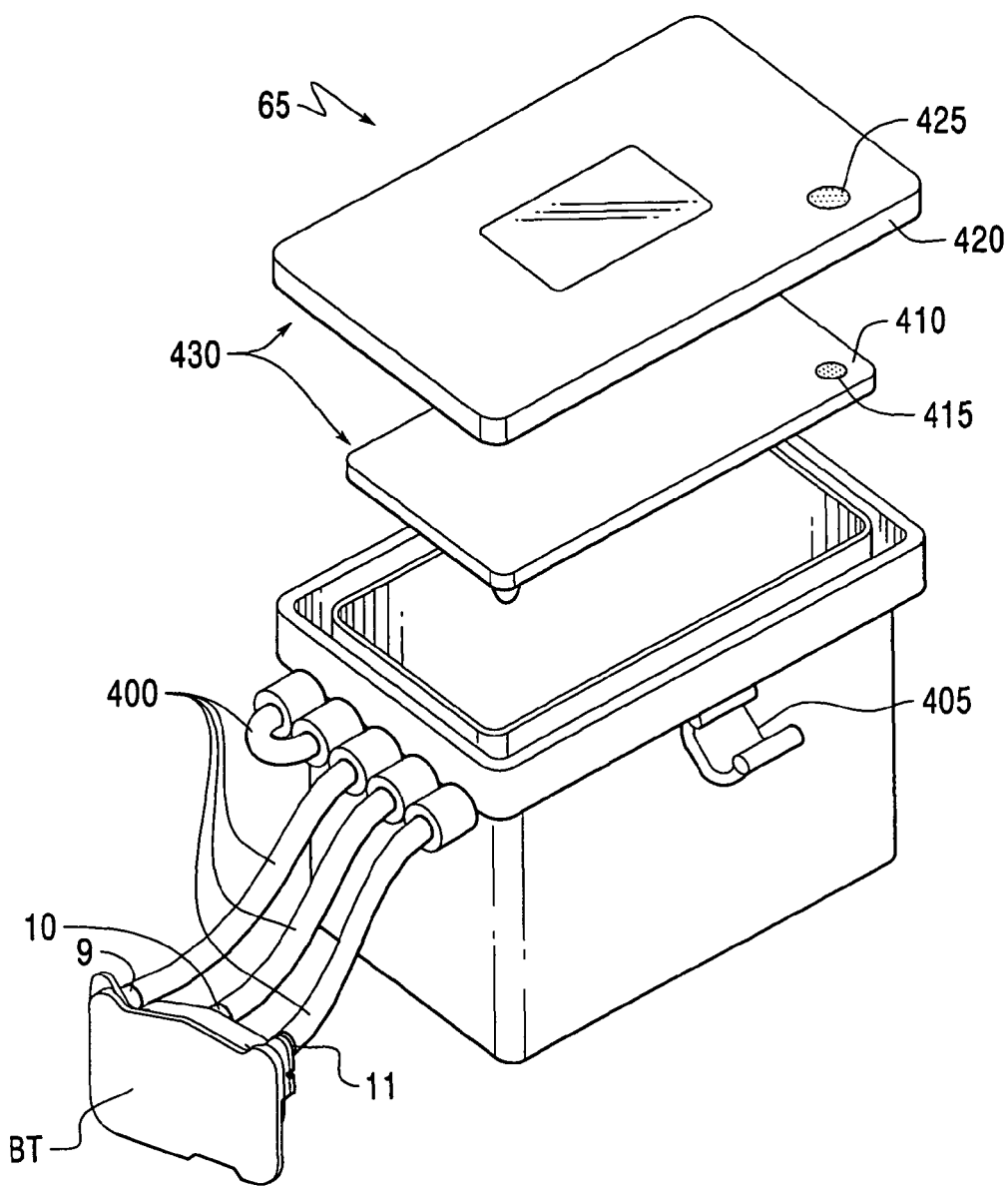
FIGS. 2A and 2B show an embodiment of an organ cassette of the present invention.
Figure 2B:
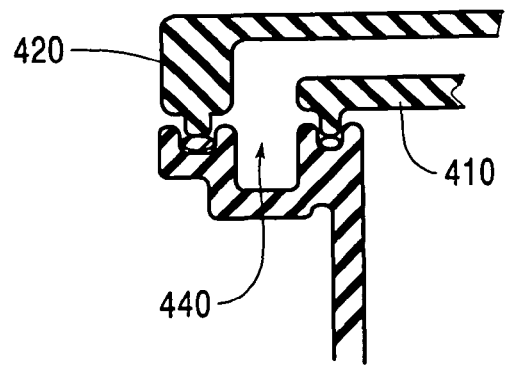

FIGS. 2A and 2B show an alternative embodiment of cassette 65. In FIG. 2A, cassette 65 is shown with tubeset 400. Tube set 400 can be connected to an inlet tube port connector 11, bubble outlet tube port connector 10 and liquid outlet tube port connector 9 of a bubble trap device according to this invention. When the tube set 400 is connected to the bubble trap device, the cassette 65 can be readily moved between various apparatus, and preferably allows cassette 65 to be moved between various apparatus without jeopardizing the sterility of the interior of cassette 65. For example, when the cassette 65, and the accompanying tube set 400 and bubble trap device, is placed in a transporter, the tube set 400 and bubble trap device are preferably connectable to the transporter to secure the tube set 400 and bubble device to the transporter during operation. The tube set 400 and bubble trap device can also be connected to an organ perfusion, storage and/or diagnostic apparatus. Additionally, the tube set 400 can be connected to any number of devices that are connected to the perfusion, storage, diagnostic, transport and/or other apparatus.

Preferably, cassette 65 is made of a sufficiently durable material that it can withstand penetration and harsh impact. Cassette 65 is provided with a lid, preferably two lids, an inner lid 410 and an outer lid 420. The lids 410 and 420 may be removable or may be hinged or otherwise connected to the body of cassette 65. Clasp 405, for example, may provide a mechanism to secure lids 410 and 420 to the top of cassette 65. Clasp 405 may additionally be configured with a lock to provide further security and stability. A biopsy and/or venting port 430 may additionally be included in inner lid 410 or both inner lid 410 and outer lid 420. Port 430 may provide access to the organ to allow for additional diagnosis of the organ with minimal disturbance of the organ. Cassette 65 may also have an overflow trough 440 (shown in FIG. 2B). Overflow trough 440 is a channel present in the top of cassette 65. When lids 410 and 420 are secured on cassette 65, overflow trough 440 provides a region that is easy to check to determine if the inner seal is leaking. Perfusate may be poured into and out of cassette 65 and may be drained from cassette 65 through a stopcock or removable plug.

Cassette 65 and/or both lids 410 and 420 may be constructed of an optically transparent material to allow for viewing of the interior of cassette 65 and monitoring of the organ and to allow for video images or photographs to be taken of the organ. A perfusion apparatus or cassette 65 may be wired and fitted with a video camera or a photographic camera, digital or otherwise, to record the progress and status of the organ. Captured images may be made available over a computer network such as a local area network or the internet to provide for additional data analysis and remote monitoring. Cassette 65 may also be provided with a tag that would signal, e.g., through a bar code, magnetism, radio frequency, or other means, the location of the cassette, that the cassette is in the apparatus, and/or the identity of the organ to perfusion, storage, diagnostic and/or transport apparatus. Cassette 65 may be sterile packaged and/or may be packaged or sold as a single-use disposable cassette, such as in a peel-open pouch. A single-use package containing cassette 65 may also include tubeset 400.

Cassette 65 is preferably configured such that it may be removed from an organ perfusion apparatus and transported to another organ perfusion apparatus in a portable transporter apparatus, such as, for example, a conventional cooler or a portable container such as that disclosed in U.S. patent application Ser. No. 09/161,919, or U.S. Pat. No. 5,586,438 to Fahy, both of which are hereby incorporated by reference in their entirety.

Figure 1C:
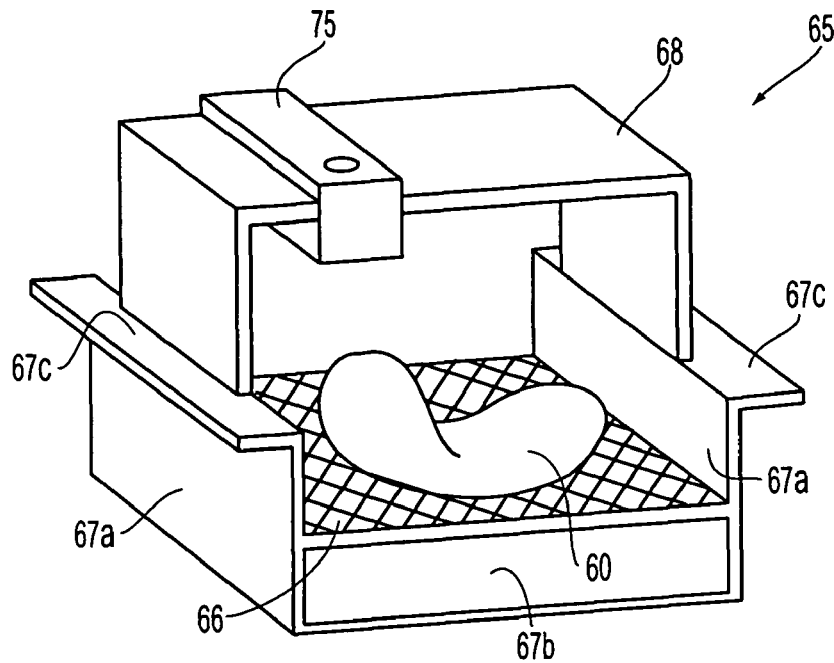
Figure 1D:
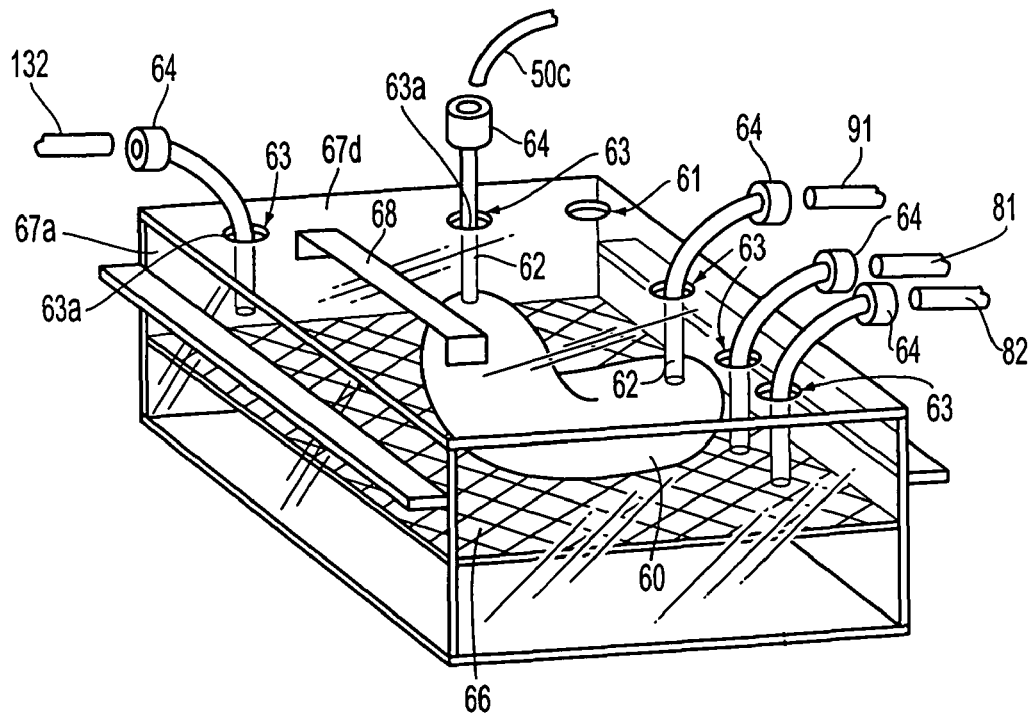

In various exemplary embodiments according to this invention, when transported, the organ may be disposed on the organ supporting surface 66 and the cassette 65 may be enclosed in a preferably sterile bag 69, as shown, for example, in FIG. 1A. When the organ is perfused with medical liquid, effluent medical liquid collects in the bag 69 to form an organ bath. Alternatively, cassette 65 can be formed with a liquid tight lower portion in which effluent medical liquid may collect, or effluent medical liquid may collect in another compartment of an organ storage, transport, perfusion and/or diagnostic apparatus, to form an organ bath. In either case, the bag 69 would preferably be removed prior to inserting the cassette into an organ storage, transporter, perfusion and/or diagnostic apparatus. Further, where a plurality of organs are to be perfused, multiple organ compartments may be provided. Alternatively, an organ in the dual-lid cassette can be transported of FIG. 2A and additionally carried within a portable organ transporter.

Figure 3:
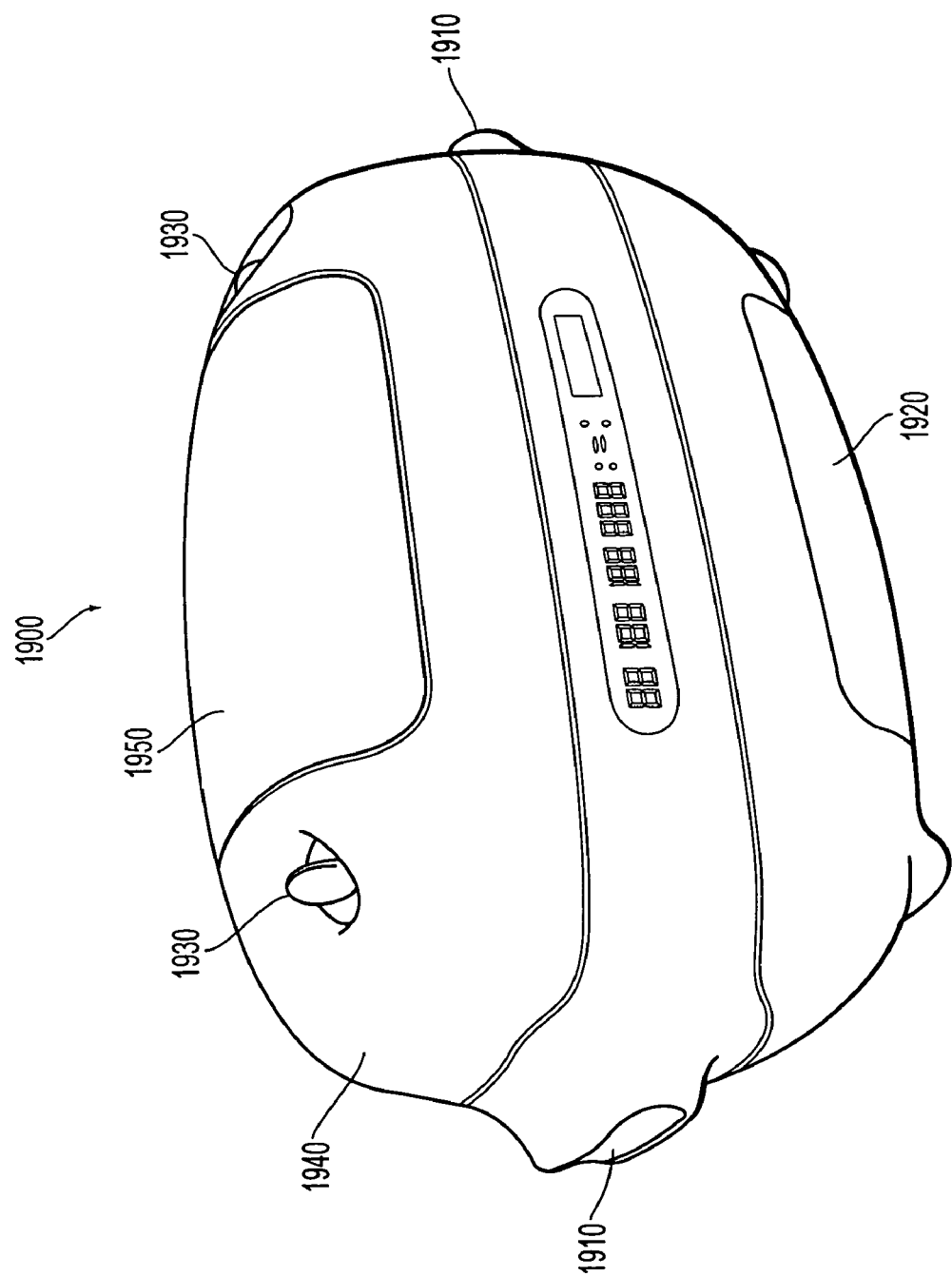
FIG. 3 shows an exterior perspective view of an organ transporter according to the present invention.

FIG. 3 shows an external view of an embodiment of transporter 1900 of the invention. The transporter 1900 of FIG. 3 has a stable base to facilitate an upright position and handles 1910 for carrying transporter 1900. Transporter 1900 may also be fitted with a shoulder strap and/or wheels to assist in carrying transporter 1900. A control panel 1920 is preferably also provided. Control panel 1920 may display characteristics, such as, but not limited to, infusion pressure, power on/off, error or fault conditions, flow rate, flow resistance, infusion temperature, bath temperature, pumping time, battery charge, temperature profile (maximums and minimums), cover open or closed, history log or graph, and additional status details and messages, some or all of which are preferably further transmittable to a remote location for data storage and/or analysis. Flow and pressure sensors or transducers in transporter 1900 may be provided to calculate various organ characteristics including pump pressure and vascular resistance of an organ, which can be stored in computer memory to allow for analysis of, for example, vascular resistance history, as well as to detect faults in the apparatus, such as elevated pressure.

Transporter 1900 preferably has latches 1930 that require positive user action to open, thus avoiding the possibility that transporter 1900 inadvertently opens during transport. Latches 1930 hold top 1940 in place on transporter 1900 in FIG. 3. Top 1940 or a portion thereof may be constructed with an optically transparent material to provide for viewing of the cassette and organ perfusion status. Transporter 1900 may be configured with a cover open detector that monitors and displays whether the cover is open or closed. Transporter 1900 may be configured with an insulating exterior of various thicknesses to allow the user to configure or select transporter 1900 for varying extents and distances of transport. In embodiments, compartment 1950 may be provided to hold patient and organ data such as charts, testing supplies, additional batteries, hand-held computing devices and/or configured with means for displaying a UNOS label and/or identification and return shipping information.

Figure 4:
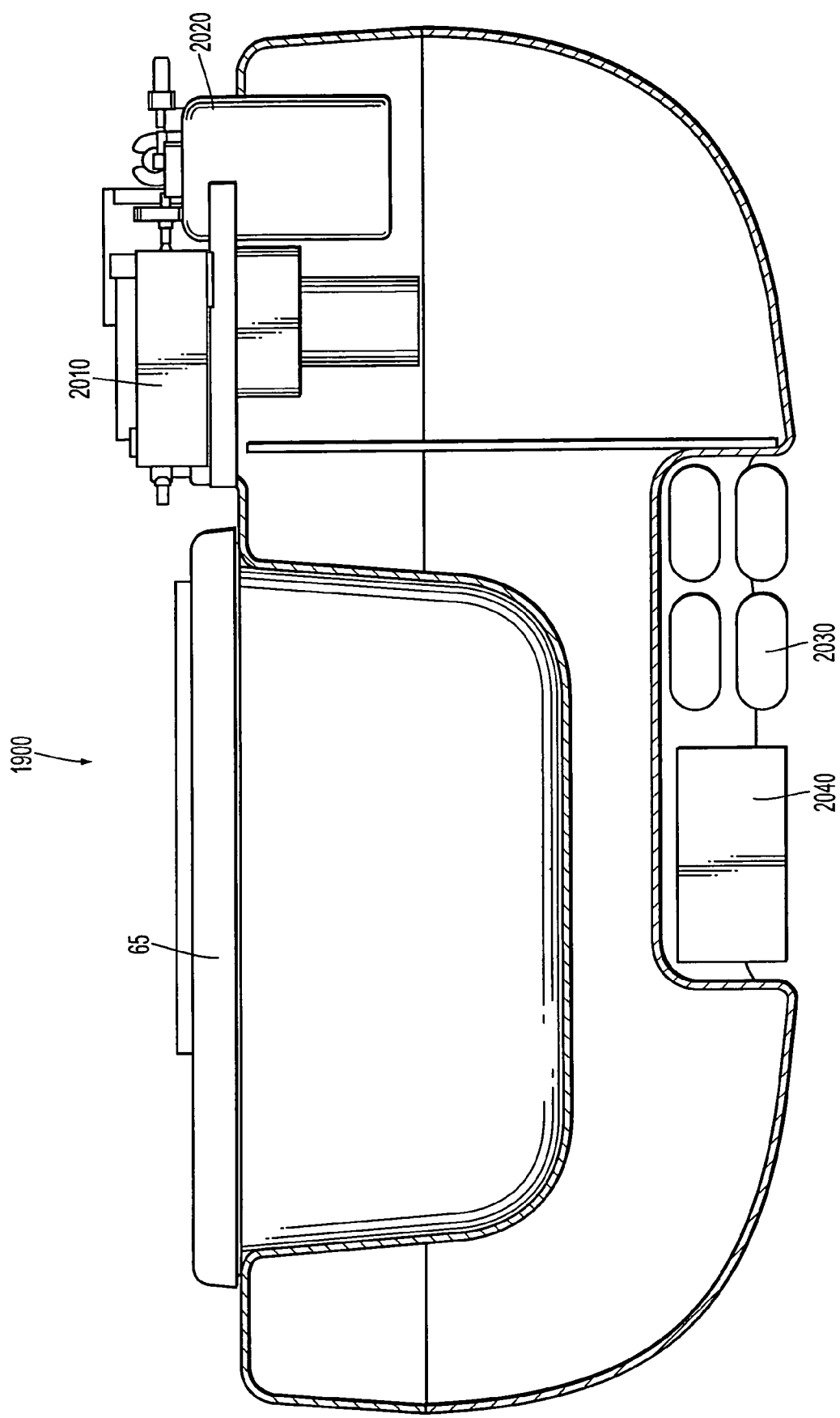
FIG. 4 shows a cross-section view of an organ transporter of FIG. 3.

FIG. 4 shows a cross-section view of a transporter 1900. Transporter 1900 contains cassette 65 and pump 2010. Cassette 65 may preferably be placed into or taken out of transporter 1900 without disconnecting tubeset 400 from cassette 65, thus maintaining sterility of the organ. In embodiments, sensors in transporter 1900 can detect the presence of cassette 65 in transporter 1900, and depending on the sensor, can read the organ identity from a barcode or radio frequency or other "smart" tag that may be attached or integral to cassette 65. This can allow for automated identification and tracking of the organ and helps monitor and control the chain of custody. A global positioning system may be added to transporter 1900 and/or cassette 65 to facilitate tracking of the organ. Transporter 1900 may be interfaceable to a computer network by hardwire connection to a local area network or by wireless communication while in transit. This interface may allow data such as perfusion parameters, vascular resistance, and organ identification and transporter and cassette location to be tracked and displayed in real-time or captured for future analysis.

Transporter 1900 also preferably contains a filter 2020 to remove sediment and other particulate matter, preferably ranging in size from 0.05 to 15 microns in diameter or larger, from the perfusate to prevent clogging of the apparatus or the organ. Transporter 1900 preferably also contains batteries 2030, which may be located at the bottom of transporter 1900 or beneath pump 2010 or at any other location but preferably one that provides easy access to change batteries 2030. Batteries 2030 may be rechargeable outside of transporter 1900 or while within transporter 1900 and/or are preferably hot-swappable one at a time. Batteries 2030 are preferably rechargeable rapidly and without full discharge. Transporter 1900 may also provide an additional storage space 2040, for example, at the bottom of transporter 1900, for power cords, batteries and other accessories. Transporter 1900 may also include a power port for a DC hookup, e.g., to a vehicle such as an automobile or airplane, and/or for an AC hookup.

Figure 5:
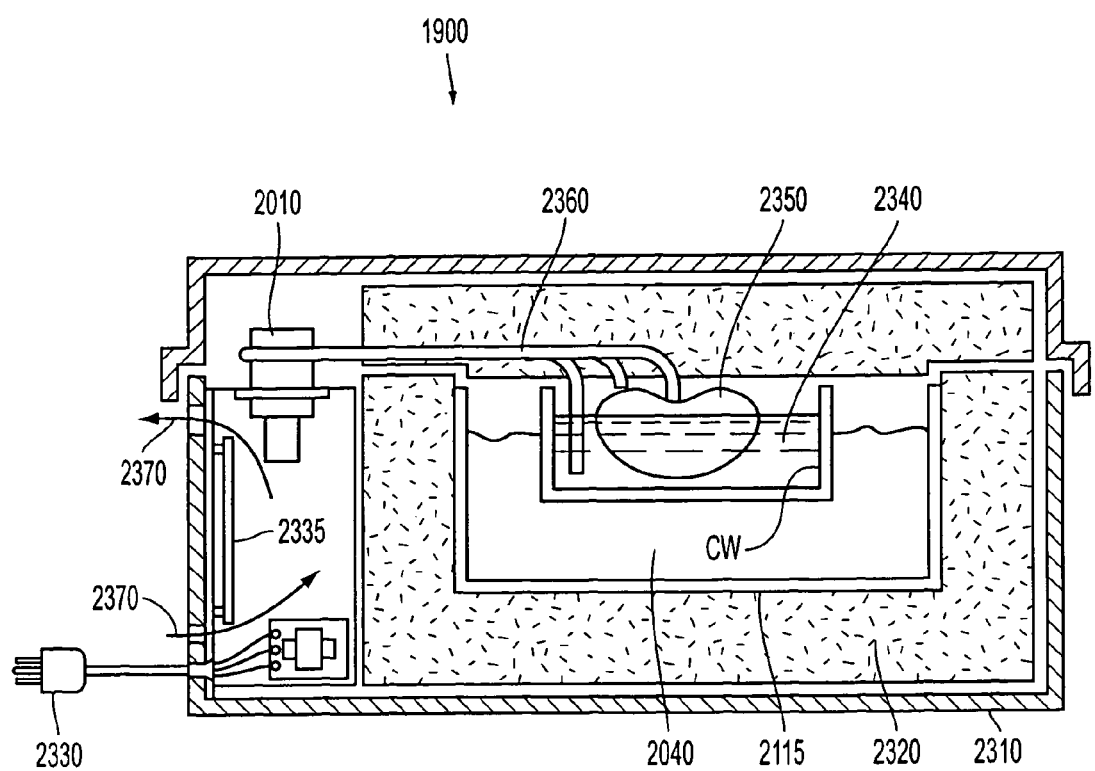
FIG. 5 shows an alternative cross-section view of an organ transporter of FIG. 3.

FIG. 5 shows an alternative cross-section of transporter 1900. In FIG. 5, the transporter 1900 may have an outer enclosure 2310 which may, for example, be constructed of metal, or preferably a plastic or synthetic resin that is sufficiently strong to withstand penetration and impact. Transporter 1900 contains insulation 2320, preferably a thermal insulation made of, for example, glass wool or expanded polystyrene. Insulation 2320 may be various thicknesses ranging from 0.5 inches to 5 inches thick or more, preferably 1 to 3 inches, such as approximately 2 inches thick. Transporter 1900 may be cooled by coolant 2110, which may be, e.g., an ice and water bath or a cryogenic material. In embodiments using cryogenic materials, the design should be such that organ freezing is prevented. An ice and water mixture is preferably an initial mixture of approximately 1 to 1, however, in embodiments the ice and water bath may be frozen solid. Transporter 1900 can be configured to hold various amounts of coolant, preferably up to 10 to 12 liters. An ice and water bath is preferable because it is inexpensive and generally can not get cold enough to freeze the organ. Coolant 2110 preferably lasts for a minimum of 6 to 12 hours and more preferably lasts for a minimum of 30 to 50 hours without changing coolant 2110. The level of coolant 2110 may, for example, be viewed through a transparent region of transporter 1900 or be automatically detected and monitored by a sensor. Coolant 2110 can preferably be replaced without stopping perfusion or removing cassette 65 from transporter 1900. Coolant 2110 is preferably maintained in a watertight compartment 2115 of transporter 1900. Compartment 2115 preferably prevents the loss of coolant 2110 in the event transporter 1900 is tipped or inverted. Heat is conducted from the walls of the perfusion reservoir and cassette 65 into coolant 2110 enabling control within the desired temperature range. Coolant 2110 is a failsafe cooling mechanism because transporter 1900 automatically reverts to cold storage in the case of power loss or electrical or computer malfunction. Transporter 1900 may also be configured with a heater to raise the temperature of the perfusate.

Transporter 1900 may be powered by batteries or by electric power provided through plug 2330. An electronics module 2335 may be provided in transporter 1900. Electronics module 2335 may be cooled by vented air convection 2370, and may further be cooled by a fan. Preferably, electronic module 2335 is positioned separate from the perfusion tubes to prevent the perfusate from wetting electronics module 2335 and to avoid adding extraneous heat from electronics module 2335 to the perfusate. Transporter 1900 preferably has a pump 2010 that provides pressure to perfusate tubing 2360 to deliver perfusate 2340 to organ 2350. Transporter 1900 may be used to perfuse various organs such as a kidney, heart, liver, small intestine and lung. Transporter 1900 and cassette 65 may accommodate various amounts of perfusate 2340, for example up to 3 to 5 liters. Preferably, approximately 1 liter of a hypothermic perfusate 2340 is used to perfuse organ 2350.

Cassette 65 and transporter 1900 are preferably constructed to fit or mate such that efficient heat transfer is enabled. The geometric elements of cassette 65 and transporter 1900 are preferably constructed such that when cassette 65 is placed within transporter 1900, the elements are secure for transport.

Figure 6:
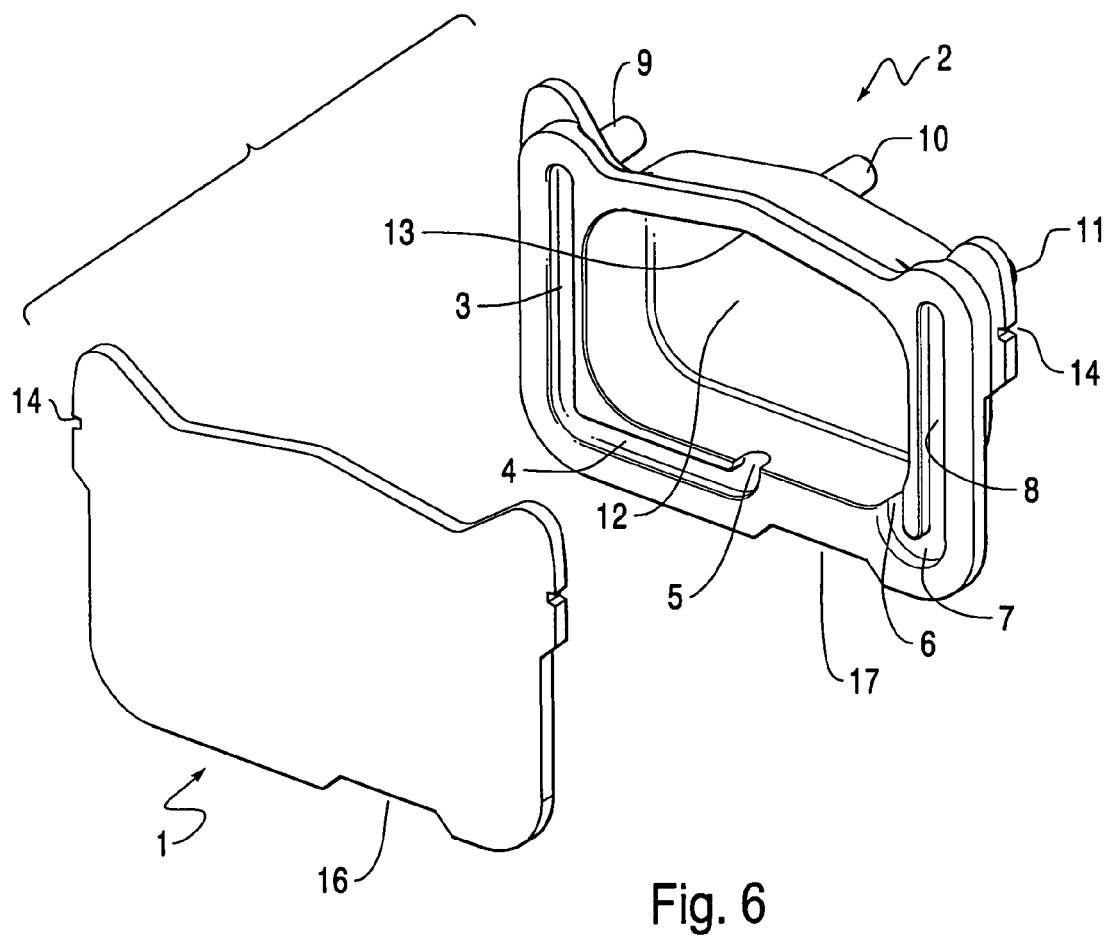
FIG. 6 shows an exploded view of the housing and cover of a bubble trap device of the invention from the rear.
Figure 7:
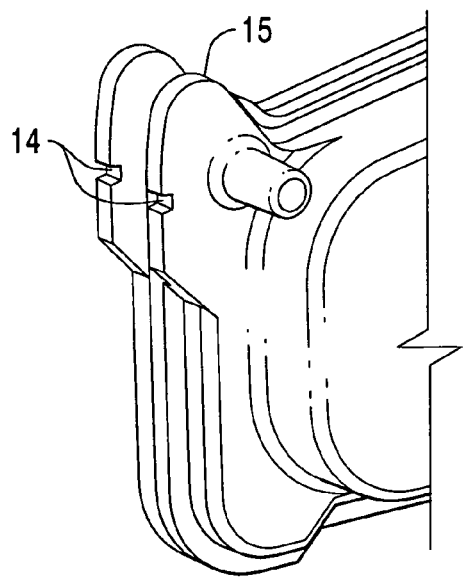
FIG. 7 shows a close-up view of a mounting slot and snap receiver of a bubble trap device according to the invention.
Figure 8:
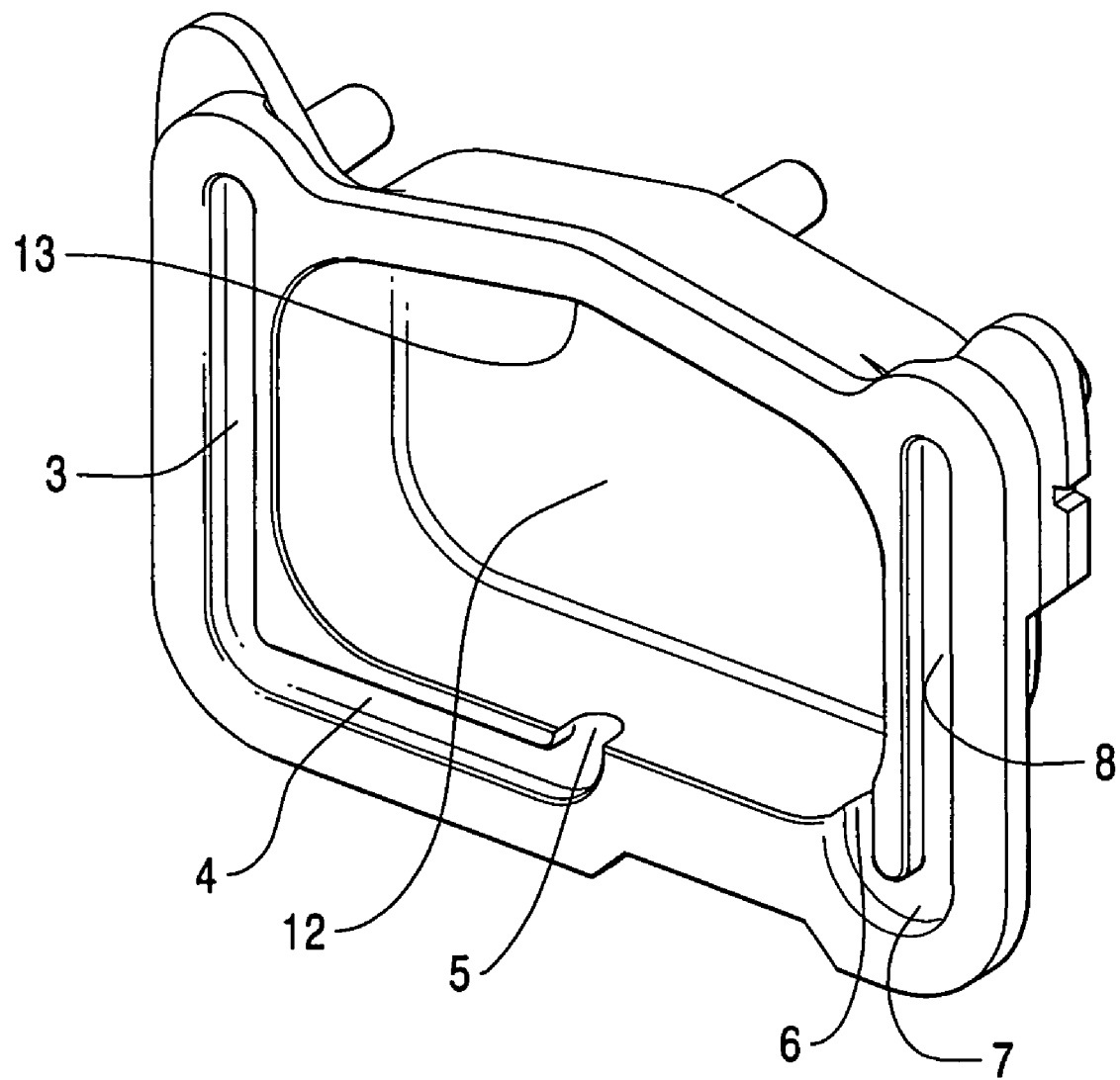
FIG. 8 shows an enlarged view of the interior of the housing of a bubble trap device according to the invention.

FIGS. 6-8 show the housing 2 and the housing cover 1 which, together make up a bubble trap device of the invention. The bubble trap device is designed and configured for connection to and use with the tube set 400 discussed above with respect to FIG. 2A. The housing 2 and/or the cover 1 of the bubble trap device may be constructed of an optically clear material to allow for viewing of the interior of the bubble trap device, monitoring liquid located therein, and/or helping an infra-red temperature sensor measure the temperature of the perfusate.

The housing 2 of the bubble trap device is connected in line with a liquid path by way of inlet tube port connector 11, bubble outlet tube port connector 10 and liquid outlet tube port connector 9. Inlet tube port connector 11 is the primary path of ingress of liquid into the vertical entrance channel 8. The vertical entrance channel 8 is preferably located in the housing 2 and connected to the entrance turn around channel 7 which is connected to the entrance separation chamber 6. The entrance separation chamber 6 is connected to an opening in the separation chamber 12. Accordingly, when housing 2 and housing cover 1 are secured together, liquid flowing into the housing will flow through the vertical entrance channel 8, entrance turn around channel 7, and entrance separation chamber 6 before reaching the separation chamber 12.

When liquid and gas flow out of chamber 12, there are two paths of exit. Gas can flow out of the bubble outlet tube port connector 10. Liquid will leave the separation chamber 12 through a liquid exit separation chamber 5. The liquid and/or gas will then flow through the horizontal liquid channel exit 4 and then through the vertical channel exit 3 before exiting from the housing 2 by way of the liquid outlet tube port connector 9. When gas flows out of the bubble outlet tube port connector 10, it will first flow from the separation chamber 12 through the outlet port 13 before exiting out through the bubble outlet tube port connector 10. It should be appreciated that the orientation of the channels located within the housing 2 can be configured in any manner as long as they provide a channel for the passage of the liquid and gas. For example, the vertical entrance channel 8 can be situated in a less than vertical manner.

The inlet tube port connector 11, the bubble outlet tube port connector 10 and the liquid outlet tube port connector 9 can provide a connection between the tube set 400 and the bubble trap device.

According to exemplary embodiments of this invention, the selected exit path may be controlled by opening and closing flow valves. During operation, a sensor (i.e., an ultrasonic sensor) associated with the inlet tube port connector 11 may detect the presence of bubbles. Preferably a liquid outlet tube port valve (not shown) associated with liquid outlet tube port connector 9 is open as the separation chamber 12 collects gas from bubbles. The captured gas may be expelled from separation chamber 12 by opening a valve (not shown) associated with the bubble outlet tube port 10 while closing the valve associated with the liquid outlet tube port connector 9. It should be appreciated that this operation may be performed at preset time intervals or in response to a signal, such as a signal from a sensor, such as an optical or ultrasonic inlet tube port sensor, that manipulates the valves. The sensor may be any known or later developed sensor which is capable of performing the above discussed operation. A sensor may be associated with the liquid outlet tube port connector 9 to detect the presence of bubbles, whereby a signal can be sent to the control panel 1920 of transporter 1900 that will stop pump 2010 until a user corrects the problem.

Figure 9:
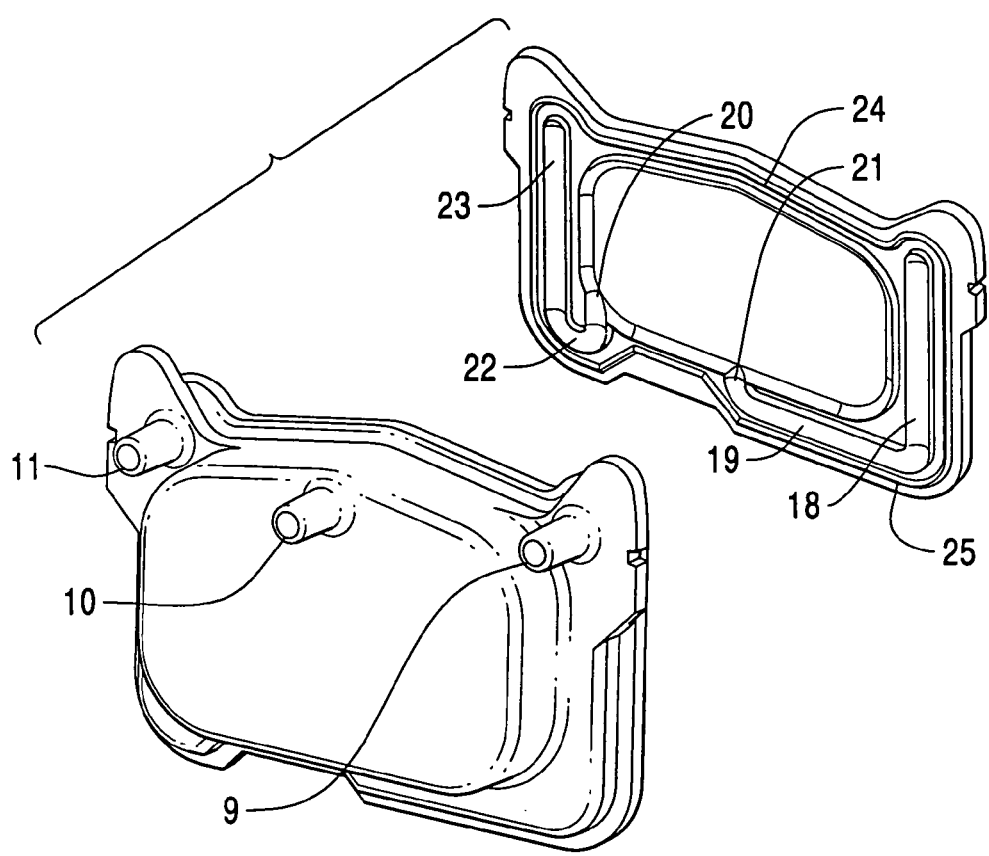
FIG. 9 shows an exploded view of the housing and cover of a bubble trap device of the invention from the front.
Figure 10:
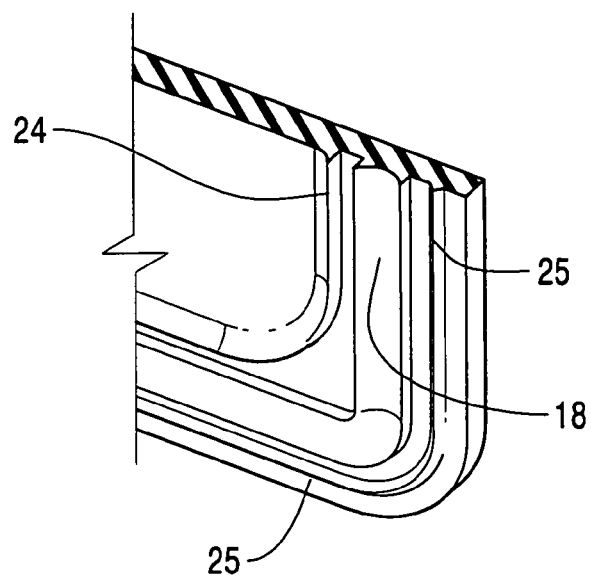
FIG. 10 shows a cross-sectional view of the cover of FIG. 9.
Figure 11:
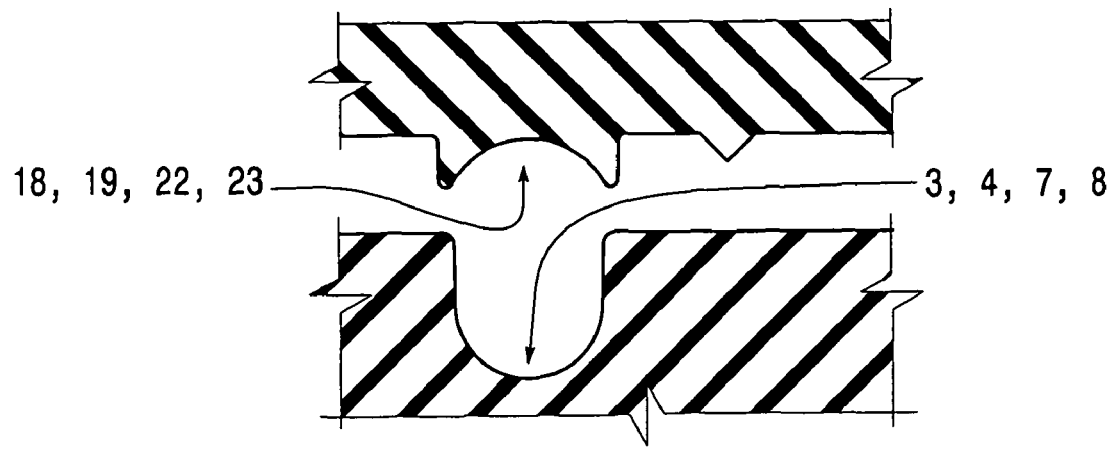
FIG. 11 shows a cross-sectional view of the housing to cover interface of a bubble trap device according to the invention.

FIGS. 9-11 show a preferred mating geometry between a housing 2 and cover 1. The mating of the housing 2 and cover 1 provides a preferred way to form the entrance vertical channel 8, the entrance turn around channel 7, the liquid exit vertical channel 3 and the horizontal liquid channel exit 4. In addition, the mating can form the separation chamber 12. After mating the housing 2 and cover 1, the inlet entrance vertical channel 8 and entrance turn around channel 7 receive the outlet vertical channel protrusion 23 and outlet turn around channel protrusion 22, respectively. Similarly, the liquid exit vertical channel 3 and the horizontal liquid channel exit 4 and outlet channels receive vertical liquid outlet channel protrusion 18 and horizontal liquid outlet channel protrusion 19. The mating of channels 3, 4, 7, and 8 with protrusions 18, 19, 22, and 23 form a passageway, preferably of cylindrical cross-section, normal to the direction of liquid flow, as best seen in FIG. 11. The mating configurations are preferably configured to minimize the potential for emboli entrapment by substantially eliminating sharp corners.

A similar mating feature can exist between the separation chamber 12 and the separation chamber protrusion 21. The mating between the housing 2 and the cover 1, and the accompanying channels 3, 4, 7, and 8 and protrusions 18, 19, 22, and 23, can provide a sealed liquid path due to an interference fit between mating side walls of the housing 2 and the cover 1. This is especially preferred if the primary hermetic seal for the device is formed by ultrasonically welding the housing and cover together. The cover 1 can contain an ultrasonic energy director 25. The ultrasonic energy director 25 melts when placed against the housing and exposed to the energy and pressure of the ultrasonic welder. It should be appreciated that any method of hermetically sealing the device is within the scope of the invention.

The assembled bubble trap device is preferably provided with a feature for aligning, locating and/or fixing the bubble trap device to one or more additional components, such as a tube frame set (not shown). A mounting alignment slot 15, for example, may be formed in the housing 2 and/or the cover 1 upon mating of the housing 2 and cover 1 to form the assembled bubble trap device, as best seen in FIG. 7. The mounting alignment slot 15 may provide a location in two axes, allowing the bubble trap device to be translated through a third axis. A mounting receiver notch 14 may be located in the direction of a third axis and receive a snap protrusion or similar device located on a mating component. Other methods can also be used to provide a connection between the bubble trap device and at least one other additional component.

Figure 12:
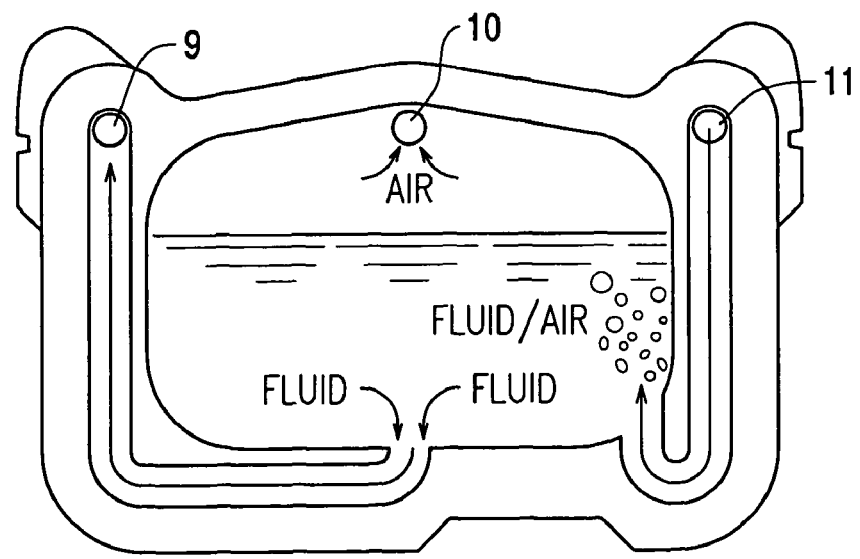
FIG. 12 shows a diagram of the liquid and gas path within a bubble trap device according to the invention.

FIG. 12 shows an exemplary embodiment of a bubble trap device according to this invention. In FIG. 12, the bubble trap device is configured with the inlet tube port connector 11 located on substantially the same plane as the bubble outlet tube port connector 10 and the liquid outlet tube port connector 9. Having substantially single plane ingress and egress ports for liquid and air flow allows for easier connection of the bubble trap device with the tubeset 400. Additionally, substantially single plane ingress and egress ports provides for easier manufacturing assembly processes of the bubble trap device. The substantially single plane orientation of the inlet tube port connector 11, the bubble outlet tube port connector 10 and the liquid outlet tube port connector 9, inter alia, permits connecting tubing, such as tube set 400, to reside in a substantially single plane without bending or twisting of the tubes in tube set 400. It also facilitates the tiltability of the device as discussed below.

In various exemplary embodiments, the inlet tube port connector 11, the bubble outlet tube port connector 10 and the liquid outlet tube port connector 9 can be positioned at various other locations on housing 2. For example, at least one of the inlet tube port connector 11, the bubble outlet tube port connector 10 and the liquid outlet tube port connector 9 can be can be located on one or more of the sides, top, or bottom of the housing 2. Additionally, any one of the connectors 9, 10, 11 can be oriented at an angle other than ninety degrees or normal to the surface of the housing 2. It should be appreciated that the inlet tube port connector 11, the bubble outlet tube port connector 10 and the liquid outlet tube port connector 9 can be provided at any location or orientation on the housing 2 that allows appropriate ingress and egress of liquid and gas between channels 3, 4, 7, and 8 and the separation chamber 12 within the bubble trap device.

Figure 13:
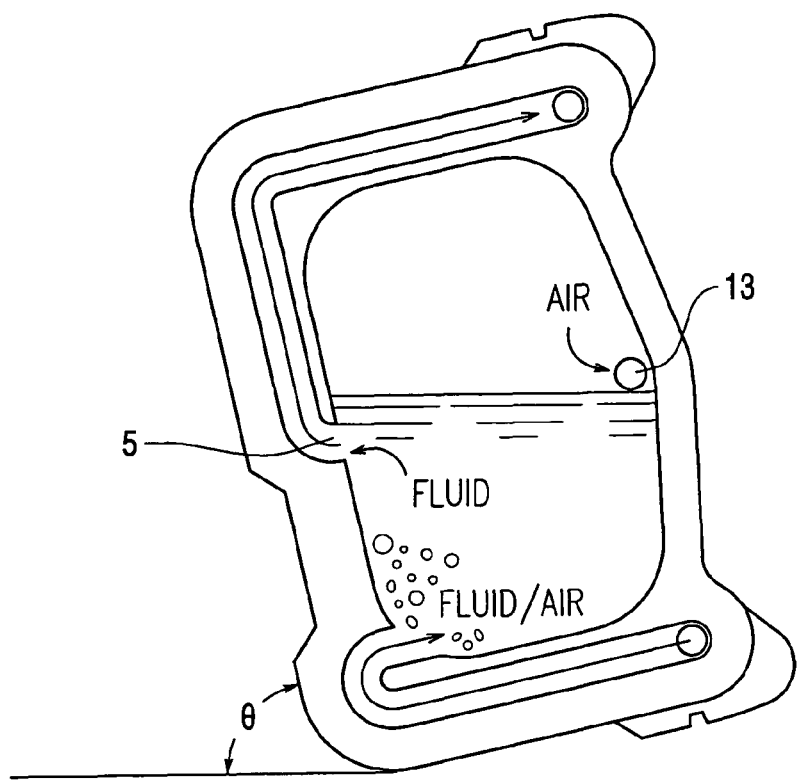
FIG. 13 shows a diagram of the bubble trap device of FIG. 12 tilted clockwise.
Figure 14:
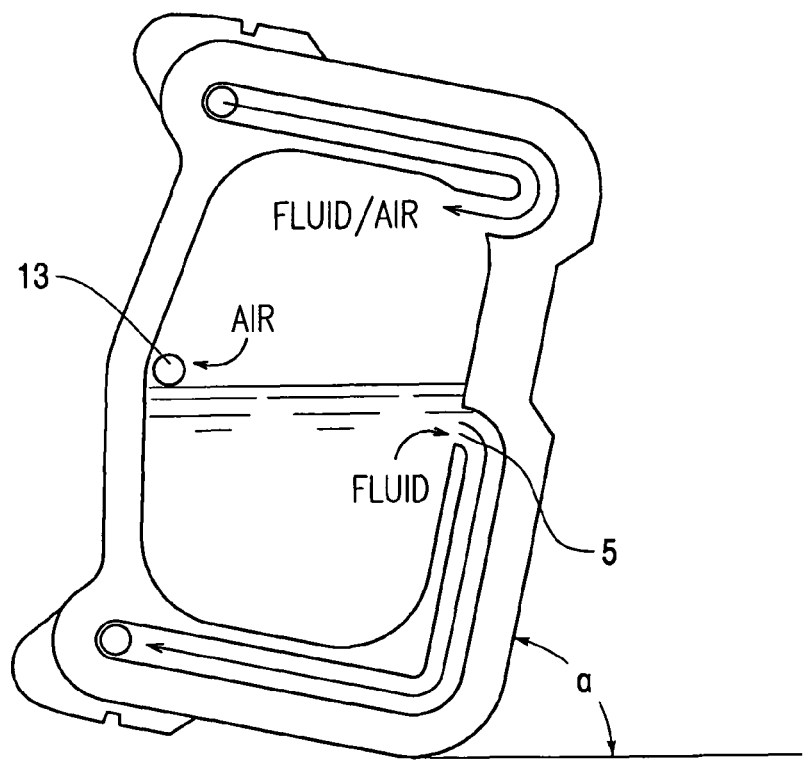
FIG. 14 shows a diagram of the bubble trap device of FIG. 12 tilted counter-clockwise.

FIGS. 13 and 14 show the advantageous range of tilt of preferred embodiments of the bubble trap device. This bubble trap device is designed with the liquid exit separation point 5 in approximately the center of separation chamber 12 and approximately opposite outlet port 13. This location of features allows the bubble trap device to be tilted at various angles θ and α, depending on selection of liquid level and port locations, and can permit tilting at various angles including, for example, up to about 90, for example 90, 89, 88, 87, ..., 1 degree, approximately 45-90, e.g., up to 70, degrees from side-to-side and front to back. It should be appreciated that the angle of tilt could increase or decrease depending on the amount of liquid and gas located within separation chamber 12. The large angle of tilt for the bubble trap device is especially desirable in embodiments associated with an organ transporter or the like, which may undergo substantial tilting during handling and transportation. When the bubble trap device is connected to the tube set 400, the large acceptable angle of tilt ensures that the bubble trap device functions when the cassette and transporter are not completely horizontal.

Figure 15:
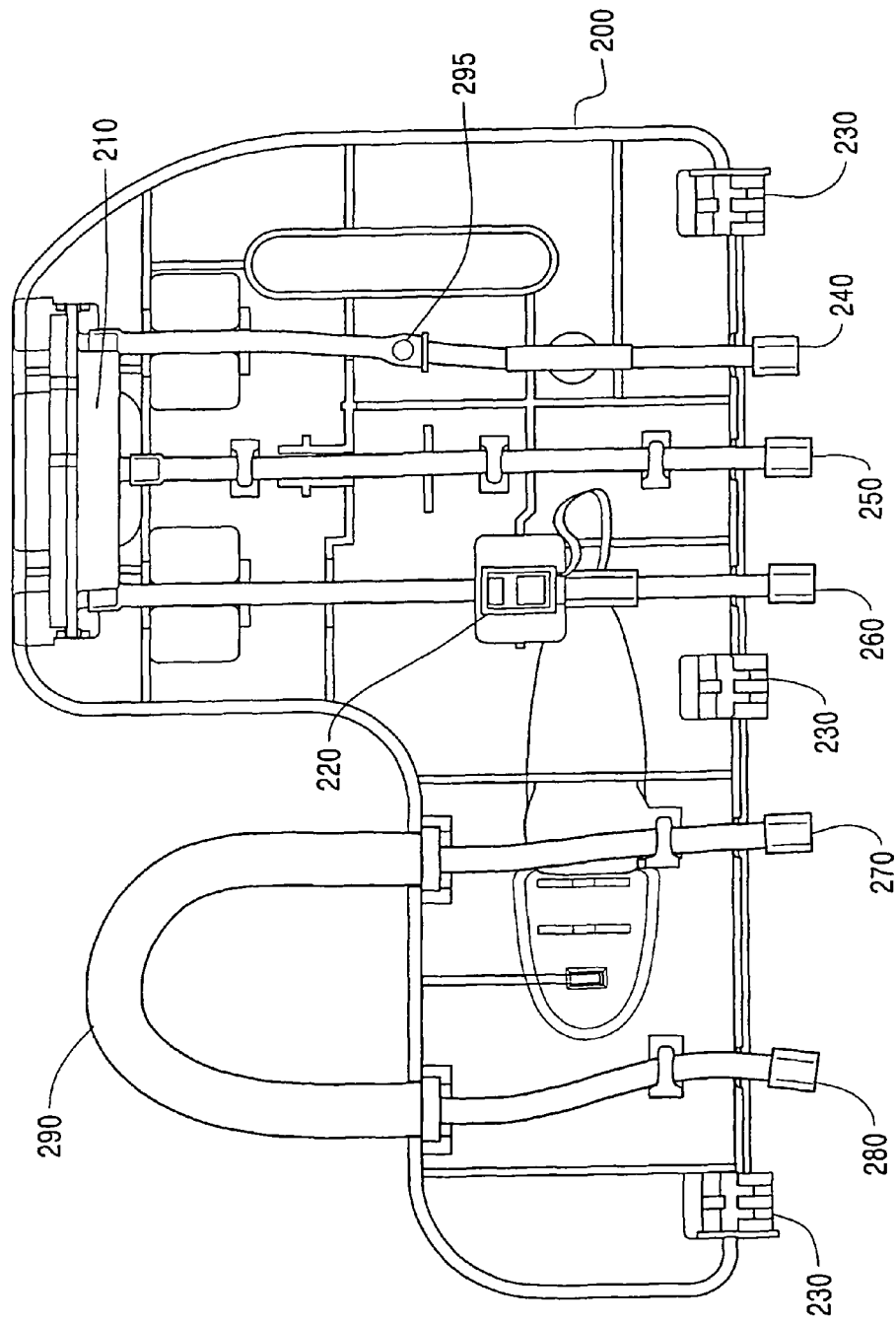
FIG. 15 shows a tube frame for holding a tube frame and the bubble trap according to the invention.

FIG. 15 shows a tube frame 200 of embodiments of the invention. The tube frame, may be used for holding tube set 400 discussed with respect to FIG. 2A. The tube frame 200 is preferably formed of a material that is light but durable, such as for example plastic, so that tube frame 200 is highly portable. The tube frame 200 is designed to hold the tubing of the tube set 400 in desired positions. In FIG. 15, tube frame 200 is shown holding the tubes of tube set 400 of FIG. 2A. It should be appreciated that there may be other numbers of tubes that comprise tube set 400. Having the tubing in set positions allows for easier installation and connection with devices such as cassette 65 as shown in FIG. 12. The cassette 65 and tube frame 200 are then preferably mated with transporter 1900.

When tube frame 200 is mated with cassette 65, the tube set 400 is preferably already connected with the cassette 65. For example, tube 270 provides an inlet to a pump 2010 from the stored liquid at the bottom of cassette 65. The liquid travels through tube 290 and back out outlet 280 through a filter which may, for example, be located inside or outside, for example, below, cassette 65. After traveling through the filter, the liquid will travel to tube 240 and into the bubble trap 210. A sample port 295 may be provided with tube frame 200 to allow for drawing liquid out of or injecting liquid into the tube 240. Liquid travels into the bubble trap 210 in tube 240 and travels out of bubble trap 210 in tube 260, which carries the liquid into the cassette, for example, to infuse and/or wash the organ. Tube 250 will carry liquid or gas leaving the bubble trap 210 into cassette 65 bypassing infusion of, but optionally washing, the organ.

It should be appreciated that tube frame 200 can hold other devices in addition to tubes. For example, tube frame 200 can hold a bubble trap device 210 and a pressure sensor 220 used to control pump 2010. It should also be appreciated that tube frame 200 and tube set 400 can be connected to a variety of devices such as the organ perfusion device 1 or an organ diagnostic device, as well as a cassette and/or transporter.

In various exemplary embodiments, tube frame 200 is preferably attachable to a portion of the transporter 1900. The tube frame 200 may be connected to transporter 1900, and other devices, by way of snaps 230 or other structure that will securely hold the tube frame to the device. Sensors, for example mechanical or electrical sensors, in transporter 1900, or other devices, can be provided to detect the presence of tube frame 200 in transporter 1900. If the tube frame 200 is not properly attached to the transporter, the sensors may be configured to send an appropriate alert message to control panel 1920 for notifying the user of a problem. If no action is taken to properly attach tube frame 200 in a given amount of time automatically set or programmed by the user, transporter 1900 can be programmed to prevent the beginning of perfusion. It should be appreciated that if perfusion has begun and tube frame 200 is not appropriately set, the transporter can be programmed to stop perfusion.

Another valuable feature of the tube frame is that makes the stationary surface for the tube 250, and tube 260. These tubes are used to route perfusion solution either directly to the organ or, bypassing the organ, into the reservoir. It is desirable to have tube 250 and tube 260 located in a relatively fixed position so that the routing may be done by pinching the tubing so that no liquid can pass. The tubes may, for example, be pinched by a solenoid (not shown) located on transporter 1900 that drives a blade that pinches tube 250 and/or tube 260 against the tube frame 200.

The above described apparatus and method of the bubble trap device, cassette and transporter may be used for child or small organs as well as for large or adult organs with modifications as needed of the cassette. The organ cassette can be configured to the shapes and sizes of specific organs or organ sizes.

While the invention has been described in conjunction with specific embodiments thereof, it is evident that many alternatives, modifications and variations may be apparent to those skilled in the art. Accordingly, the embodiments of the invention as set forth herein are intended to be illustrative, not limiting. Various changes may be made without departing from the spirit and scope of the invention.

What is claimed is:

1. An apparatus for separating gas from a liquid path, comprising:
    a chamber housing defining a chamber capable of holding at least one of liquid and gas, the chamber having a top wall, a bottom wall and side walls, the relative direction of the walls of the chamber being defined when the apparatus is in an at rest position, the chamber comprising:
        a first chamber opening in one of the walls configured to allow at least one of gas and liquid to enter the chamber;
        a second chamber opening in one of the walls configured to allow at least gas to exit the chamber, the second chamber opening being located in a middle portion in a length of a top portion of the chamber when the apparatus is in the at rest position; and
        a third chamber opening in one of the walls configured to allow liquid to exit the chamber, the third chamber opening being located in a middle portion of a bottom portion of the chamber when the apparatus is in the at rest position; and
    a plurality of channels being formed within the housing, each of the plurality of channels being in fluid communication with one of the first chamber opening, the second chamber opening and the third chamber opening,
    wherein the chamber is structured to allow uninhibited fluid communication between the first, second and third chamber openings, and
    the second and third chamber openings are located relative to one another such that when the apparatus is tilted at any angle up to 70° in any direction with respect to the at rest position, the second chamber opening remains above the third chamber opening.

2. The apparatus of claim 1, wherein the housing includes at least one connection device, wherein the at least one connection device allows connection with at least one of a tube frame, an organ or tissue transporter, an organ or tissue perfusion apparatus, and an organ or tissue diagnostic device.

3. The apparatus of claim 1, wherein at least a part of the housing is transparent.

4. The apparatus of claim 1, wherein the first chamber opening is located in the bottom portion of the chamber.

5. The apparatus of claim 1, further comprising:
a perfusion circuit connected to the chamber, and a liquid in the perfusion circuit and chamber in a quantity sufficient to fill the chamber to a level that is lower than the second chamber opening when the apparatus is on a level support.

6. The apparatus of claim 1, wherein the housing includes at least first, second and third housing openings.

7. The apparatus of claim 6, wherein the first housing opening is in fluid communication with the first chamber opening, the second housing opening is in fluid communication with the second chamber opening, and the third housing opening is in fluid communication with the third chamber opening.

8. The apparatus of claim 7, wherein the plurality of channels includes an entrance channel having a first end and a second end, wherein the first end is in fluid communication with the first housing opening and the second end is in fluid communication with the first chamber opening.

9. The apparatus of claim 7, wherein the plurality of channels includes an exit channel having a first exit channel end and a second exit channel end, wherein the first exit channel end is in fluid communication with the third chamber opening and the second exit channel end is in fluid communication with the third housing opening.

10. The apparatus of claim 6, wherein tubing is connectible to each of the housing openings to be in fluid communication with the housing openings.

11. The apparatus of claim 10, further comprising a sensor, wherein the sensor is capable of detecting a gas in the tubing connectible to at least one of the first and third housing openings.

12. The apparatus of claim 11, further comprising a flow control valve associated with the third housing opening, wherein the flow control valve prevents liquid from exiting the chamber through tubing connectible to the third housing opening when gas is detected.

13. The apparatus of claim 12, further comprising a flow control valve associated with the tubing connected to the second housing opening, wherein the flow control valve is open when gas is detected to allow gas to leave the chamber.

14. The apparatus of claim 11, wherein the sensor is an ultrasonic sensor.

15. The apparatus of claim 11, further comprising a pump for moving the at least one of liquid and gas through the tubing, wherein the pump stops the flow of the at least one of liquid and gas into the first housing opening when the sensor detects gas in the tubing connectible to the third housing opening.

16. The apparatus of claim 10, wherein the tubing is connectible to at least one of a tube frame, an organ or tissue transporter, an organ or tissue perfusion apparatus, and an organ or tissue diagnostic device.

17. The apparatus of claim 6, further wherein:
one of the plurality of channels extends from the first chamber opening to below the chamber, turns, and connects to the first housing opening at a top portion of the housing.

18. The apparatus of claim 6, wherein one of the plurality of channels extends from the third chamber opening to below the chamber, extends along the bottom wall, turns and extends along one of the side walls, and connects to the third housing opening at a top portion of the housing.

19. The apparatus of claim 6, wherein
a first channel of the plurality of channels extends from the first chamber opening to below the chamber, turns, and connects to the first housing opening at a top portion of the housing, and
a second channel of the plurality of channels extends from the third chamber opening to below the chamber, extends along the bottom wall, turns and extends along one of the side walls, and connects to the third housing opening at a top portion of the housing.

20. An apparatus for separating gas from a liquid path, comprising:
a chamber housing defining a chamber capable of holding at least one of liquid and gas, the chamber having a top wall, a bottom wall and side walls, and the chamber comprising:
a first chamber opening in one of the walls configured to allow at least one of gas and liquid to enter the chamber;
a second chamber opening in one of the walls configured to allow at least gas to exit the chamber, the second chamber opening being located in a middle portion in a length of a top portion of the chamber; and
a third chamber opening in one of the walls configured to allow liquid to exit the chamber, the third chamber opening being located in a middle portion of a bottom portion of the chamber; and
a plurality of channels being formed within the housing, each of the plurality of channels being in fluid communication with one of the first chamber opening, the second chamber opening and the third chamber opening, wherein:
the chamber is structured to allow uninhibited fluid communication between the first, second and third chamber openings,
the housing includes at least first, second and third housing openings,
the first housing opening is in fluid communication with the first chamber opening, the second housing opening is in fluid communication with the second chamber opening, and the third housing opening is in fluid communication with the third chamber opening, and
the first and third housing openings are located on a same side wall of the housing.

21. The apparatus of claim 20, wherein the first and third housing openings are located at opposite ends of the same side wall.

22. The apparatus of claim 21, wherein the second housing opening is located on the same side wall substantially midway between the first and third openings.

23. The apparatus of claim 22, wherein the first, second and third housing openings are located at or near a top of the same side wall.

24. The apparatus of claim 23, wherein the first, second and third housing openings are oriented substantially on the same plane.

25. The apparatus of claim 20, further comprising a sensor, wherein tubing is connectible to each of the housing openings to be in fluid communication with the housing openings and the sensor is capable of detecting a gas in the tubing connectible to at least one of the first and third housing openings.

26. An apparatus for separating gas from a liquid path, comprising:
a chamber housing defining a chamber capable of holding at least one of liquid and gas, the chamber having a top wall, a bottom wall and side walls, and the chamber comprising:
a first chamber opening in one of the walls configured to allow at least one of gas and liquid to enter the chamber;
a second chamber opening in one of the walls configured to allow at least gas to exit the chamber, the second chamber opening being located in a middle portion in a length of a top portion of the chamber; and
a third chamber opening in one of the walls configured to allow liquid to exit the chamber, the third chamber opening being located in a middle portion of a bottom portion of the chamber; and
a plurality of channels being formed within the housing, each of the plurality of channels being in fluid communication with one of the first chamber opening, the second chamber opening and the third chamber opening, wherein:
the chamber is structured to allow uninhibited fluid communication between the first, second and third chamber openings,
the housing includes at least first, second and third housing openings,
the first housing opening is in fluid communication with the first chamber opening, the second housing opening is in fluid communication with the second chamber opening, and the third housing opening is in fluid communication with the third chamber opening,
the plurality of channels includes an entrance channel having a first end and a second end, wherein the first end is in fluid communication with the first housing opening and the second end is in fluid communication with the first chamber opening, and
the first housing opening is located at or near the top portion of the housing and the first chamber opening is at or near the bottom portion of the chamber.

27. The apparatus of claim 26, wherein at least a portion of the entrance channel is approximately vertical.

28. The apparatus of claim 27, wherein the approximately vertical portion of the channel extends approximately a height of the chamber.

29. The apparatus of claim 27, wherein at least a portion of the entrance channel near the second end is curved.

30. The apparatus of claim 26, further comprising a sensor, wherein tubing is connectible to each of the housing openings to be in fluid communication with the housing openings and the sensor is capable of detecting a gas in the tubing connectible to at least one of the first and third housing openings.

31. An apparatus for separating gas from a liquid path, comprising:
a chamber housing defining a chamber capable of holding at least one of liquid and gas, the chamber having a top wall, a bottom wall and side walls, and the chamber comprising:
a first chamber opening in one of the walls configured to allow at least one of gas and liquid to enter the chamber;
a second chamber opening in one of the walls configured to allow at least gas to exit the chamber, the second chamber opening being located in a middle portion in a length of a top portion of the chamber;
a third chamber opening in one of the walls configured to allow liquid to exit the chamber, the third chamber opening being located in a middle portion of a bottom portion of the chamber; and
a plurality of channels being formed within the housing, each of the plurality of channels being in fluid communication with one of the first chamber opening, the second chamber opening and the third chamber opening, wherein:
the chamber is structured to allow uninhibited fluid communication between the first, second and third chamber openings,
the housing includes at least first, second and third housing openings,
the first housing opening is in fluid communication with the first chamber opening, the second housing opening is in fluid communication with the second chamber opening, and the third housing opening is in fluid communication with the third chamber opening,
the plurality of channels includes an exit channel having a first exit channel end and a second exit channel end, wherein the first exit channel end is in fluid communication with the third chamber opening and the second exit channel end is in fluid communication with the third housing opening, and
at least a portion of the exit channel is approximately horizontal and the third chamber opening is in fluid communication with the approximately horizontal portion of the exit channel by the first end of the exit channel.

32. The apparatus of claim 31, wherein at least a portion of the exit channel is approximately vertical and one end of the approximately vertical portion is in fluid communication with the approximately horizontal portion and another end of the substantially vertical portion is in fluid communication with the third housing opening.

33. The apparatus of claim 32, wherein the approximately vertical and horizontal portions are connected by a curved portion of the exit channel.

34. The apparatus of claim 31, wherein the approximately horizontal portion of the exit channel extends approximately the length of the bottom wall of the chamber.

35. The apparatus of claim 32, wherein the approximately vertical portion of the exit channel extends approximately the height of a side wall of the chamber.

36. The apparatus of claim 31, further comprising a sensor, wherein tubing is connectible to each of the housing openings to be in fluid communication with the housing openings and the sensor is capable of detecting a gas in the tubing connectible to at least one of the first and third housing openings.

37. An apparatus for separating gas from a liquid path, comprising:
a chamber housing defining a chamber capable of holding at least one of liquid and gas, the chamber having a top wall, a bottom wall and side walls, and the chamber comprising:
a first chamber opening in one of the walls configured to allow at least one of gas and liquid to enter the chamber;
a second chamber opening in one of the walls configured to allow at least gas to exit the chamber, the second chamber opening being located in a middle portion in a length of a top portion of the chamber; and
a third chamber opening in one of the walls configured to allow liquid to exit the chamber, the third chamber opening being located in a middle portion of a bottom portion of the chamber; and
a plurality of channels being formed within the housing, each of the plurality of channels being in fluid communication with one of the first chamber opening, the second chamber opening and the third chamber opening, wherein the chamber is structured to allow uninhibited fluid communication between the first, second and third chamber openings, the housing includes at least first, second and third housing openings, the first housing opening is in fluid communication with the first chamber opening, the second housing opening is in fluid communication with the second chamber opening, and the third housing opening is in fluid communication with the third chamber opening, and the plurality of channels includes:

an entrance channel having a first end and a second end, wherein the first end is in fluid communication with the first housing opening located at or near a top portion of the housing and the second end is in fluid communication with the first chamber opening located at or near the bottom of the chamber, wherein at least a portion of the entrance channel is approximately vertical and extends approximately a height of the chamber and at least a portion of the entrance channel near the second end is curved; and an exit channel having a first exit channel end and a second exit channel end, wherein the first exit channel end is in fluid communication with the third chamber opening and the second exit channel end is in fluid communication with the third housing opening, wherein at least a portion of the exit channel is approximately horizontal and the third chamber opening is in fluid communication with the approximately horizontal portion of the exit channel by the first end of the exit channel, at least a portion of the exit channel is approximately vertical and one end of the approximately vertical portion is in fluid communication with the approximately horizontal portion and another end of the substantially vertical portion is in fluid communication with the third housing opening, the approximately vertical and horizontal portions are connected by a curved portion of the exit channel, wherein the approximately horizontal portion of the exit channel extends approximately ½ the length of the bottom wall of the chamber and the approximately vertical portion of the exit channel extends approximately the height of a side wall of the chamber.

38. The apparatus of claim 37, further comprising a sensor, wherein tubing is connectible to each of the housing openings to be in fluid communication with the housing openings and the sensor is capable of detecting a gas in the tubing connectible to at least one of the first and third housing openings.

39. A method for separating gas from a liquid path in a chamber housing that defines a chamber capable of holding at least one of liquid and gas, the chamber including a top wall, a bottom wall, and side walls, the relative direction of the walls of the chamber being defined when the apparatus is in an at rest position, the method comprising:

supplying at least one of liquid and gas to the chamber through a first chamber opening in one of the walls;

removing gas from the chamber through a second chamber opening in one of the walls, the second chamber opening being located in a middle portion in a length of a top portion of the chamber when the apparatus is in the at rest position;

removing liquid from the chamber through a third chamber opening in one of the walls, the third chamber opening being located in a middle portion of a bottom portion of the chamber when the apparatus is in the at rest position, maintaining enough liquid in the chamber that when the chamber is tilted at an angle up to approximately 90 degrees, only liquid leaves the chamber through the third chamber opening, wherein each of the chamber openings is in fluid communication with one of a plurality of channels formed within the chamber housing, the chamber is structured to allow uninhibited fluid communication between the first, second and third chamber openings, and the second and third chamber openings are located relative to one another such that when the apparatus is tilted at any angle up to 70° in any direction with respect to the at rest position, the second chamber opening remains above the third chamber opening.

40. The method of claim 39, wherein the chamber is structured to allow uninhibited fluid communication between the first chamber opening, the second chamber opening and the chamber third chamber opening.

41. The method of claim 40, wherein the plurality of channels includes an entrance channel having a first end and a second end, the entrance channel connecting the first chamber opening with a first housing opening in the housing, and wherein the first end is connected to the first housing opening and the second end is connected to the first chamber opening.

42. The method of claim 40, wherein the plurality of channels includes an exit channel having a first end and a second end, the exit channel connecting the third chamber opening with a third housing opening, and wherein the first exit channel end is connected to the third chamber opening and the second exit channel end is connected to a third housing opening.

43. The method of claim 42, wherein the second chamber opening is connected to a second housing opening.

44. The method of claim 43, wherein the first, second, and third housing openings are located on a same wall of the housing.

45. The method of claim 44, wherein the first, second, and third housing openings are oriented on substantially the same plane.

46. The method of claim 40, further comprising connecting the housing to at least one of a tube frame, an organ or tissue transporter, an organ or tissue perfusion apparatus, and an organ or tissue diagnostic device.

47. The method of claim 40, further comprising connecting tubing to at least one of first, second, and third housing openings.

48. The method of claim 47, further comprising detecting gas in at least one of the tubing connected to the first and third housing openings.

49. The method of claim 48, further comprising closing a flow control valve associated with the third housing opening when gas is detected, thereby effectively preventing liquid from exiting the housing through the tubing connected to the third housing opening.

50. The method of claim 49, further comprising opening a flow control valve associated with the tubing connected to the second housing opening when the flow control valve associated with the third housing opening is closed, thereby effectively removing gas from the chamber.

51. The method of claim 50, wherein the opening and closing of the flow control valves occurs at preset time intervals.

52. The method of claim 51, wherein the gas in the tubing is detected by a sensor.

53. The method of claim 52, further comprising opening and closing the flow control valves as a result of a signal sent by the sensor.

54. The method of 52, wherein the sensor is an ultrasonic sensor.

55. The method of 48, further comprising stopping the flow of the at least one of liquid and gas into the first housing opening when gas is detected is the tubing connected to the third housing opening.

56. The method of claim 47, further comprising connecting the tubing to at least one of a tube frame, an organ or tissue transporter, an organ or tissue perfusion apparatus, and an organ or tissue diagnostic device.

57. The method of claim 40, further comprising forming the housing by mating a plurality of sections.

58. The method of claim 57, further comprising melting an energy director to hermetically seal the sections.

59. The method of claim 58, wherein the energy director is melted by ultrasonic welding.

60. An apparatus for transporting an organ or tissue, comprising:
 an organ or tissue transporter;
 a chamber housing defining a chamber capable of holding at least one of liquid and gas, the chamber housing connectible to the organ transporter, the chamber having a top wall, a bottom wall and side walls capable of holding at least one of liquid and gas and the relative direction of the walls of the chamber being defined when the apparatus is in an at rest position, the chamber comprising:
  a first chamber opening in one of the walls configured to allow at least one of gas and liquid to enter the chamber;
  a second chamber opening in one of the walls configured to allow at least gas to exit the chamber, the second chamber opening being located in a middle portion in a length of a top portion of the chamber when the apparatus is in the at rest position; and
  a third chamber opening in one of the walls configured to allow liquid to exit the chamber, the third chamber opening being located in a middle portion of a bottom portion of the chamber when the apparatus is in the at rest position; and
 a plurality of channels being formed within the housing, each of the plurality of channels being in fluid communication with one of the first chamber opening, the second chamber opening and the third chamber opening,
 wherein the chamber is structured to allow uninhibited fluid communication between the first, second and third chamber openings, and
 the second and third chamber openings are located relative to one another such that when the apparatus is tilted at any angle up to 70° in any direction with respect to the at rest position, the second chamber opening remains above the third chamber opening.

61. The apparatus of claim 60, wherein
 the housing includes at least one connection device connectible to the organ transporter, and
 the chamber is structured to allow uninhibited fluid communication between the first chamber opening, the second chamber opening and the third chamber opening.

62. The apparatus of claim 61, wherein the housing includes at least first, second and third housing openings and tubing that is connectible to each of the first, second, and third housing openings.

63. The apparatus of claim 62, further comprising a sensor, wherein the sensor is capable of detecting a gas in the tubing.

64. The apparatus of claim 63, further comprising a flow control valve connectible to the organ transporter and associated with the tubing connectible to the third housing opening, wherein the flow control valve prevents liquid from exiting the chamber through tubing connectible to the third housing opening when gas is detected.

65. The apparatus of claim 63, further comprising a flow control valve connectible to the organ transporter and associated with the tubing connectible to the second housing opening, wherein the flow control valve is open when gas is detected to allow gas to leave the chamber.

66. The apparatus of claim 63, wherein the sensor is an ultrasonic sensor.

67. The apparatus of claim 63, further comprising a pump connectible to the organ transporter for moving the at least one of liquid and gas through the tubing, wherein the pump stops the flow of the at least one of liquid and gas into the first housing opening when the sensor detects gas in the tubing connectible to the third housing opening.

68. The apparatus of claim 62, wherein the housing and the tubing are connectible to a tube frame capable of holding at least a plurality of tubes, wherein the tube frame is connectible to the organ transporter.

69. The apparatus of claim 60, wherein the first chamber opening is located in the lower portion of the chamber.

70. The apparatus of claim 60, further comprising a sensor, wherein tubing is connectible to each of the channels to be in fluid communication with the chamber openings and the sensor is capable of detecting a gas in the tubing connectible to at least one of the channels.

71. An apparatus for separating gas from a liquid path, comprising:
 a chamber housing defining a chamber having a bottom, a top and side walls, the chamber housing being capable of holding at least one of liquid and gas;
  a first chamber opening configured to allow at least one of gas and liquid to enter the chamber;
  a second chamber opening configured to allow at least gas to exit the chamber;
  a third chamber opening configured to allow liquid to exit the chamber;
  a liquid at a level that is below the second chamber opening and above the third chamber opening when the apparatus is in an at rest position and when the apparatus is tilted at any angle up to 70° in any direction from the at rest position, wherein
 the first chamber opening is in one of the side walls,
 the second chamber opening is in one of the side walls and located in a middle portion in a length of an upper portion of the chamber,
 the third chamber opening is in one of the side walls and located in a middle portion of a lower portion of the chamber,
 a plurality of channels are formed within the housing, each of the plurality of channels being in fluid eon communication with one of the first chamber opening, the second chamber opening and the third chamber opening, and
 the chamber is structured to allow uninhibited fluid communication between the first, second and third chamber openings.

72. The apparatus of claim 71, further comprising a sensor, wherein tubing is connectible to each of the channels to be in fluid communication with the chamber openings and the sensor is capable of detecting a gas in the tubing connectible to at least one of the channels.

* * * * *